(12) United States Patent
Voellmy

(10) Patent No.: US 12,257,300 B2
(45) Date of Patent: Mar. 25, 2025

(54) REPLICATION-COMPETENT CONTROLLED ALPHA-HERPESVIRUS VECTORS AND USES THEREFORE

(71) Applicant: HSF Pharmaceuticals SA, La Tour-de-Peilz (CH)

(72) Inventor: Richard W Voellmy, La Tour-de-Peilz (CH)

(73) Assignee: HSF PHARMACEUTICALS S.A., La Tour-de-Peilz (CH)

( * ) Notice: Subject to any disclaimer, the term of this patent is extended or adjusted under 35 U.S.C. 154(b) by 0 days.

(21) Appl. No.: 17/300,287

(22) PCT Filed: Nov. 4, 2019

(86) PCT No.: PCT/EP2019/080138
§ 371 (c)(1),
(2) Date: May 12, 2021

(87) PCT Pub. No.: WO2020/104180
PCT Pub. Date: May 28, 2020

(65) Prior Publication Data
US 2023/0270846 A1    Aug. 31, 2023

Related U.S. Application Data

(60) Provisional application No. 62/917,066, filed on Nov. 19, 2018.

(30) Foreign Application Priority Data

Nov. 19, 2018    (EP) .................................... 18207121

(51) Int. Cl.
| | | |
|---|---|---|
| A61K 39/245 | (2006.01) | |
| A61K 39/00 | (2006.01) | |
| A61P 31/12 | (2006.01) | |
| C12N 15/86 | (2006.01) | |

(52) U.S. Cl.
CPC ........ A61K 39/245 (2013.01); A61K 39/0011 (2013.01); A61P 31/12 (2018.01); C12N 15/86 (2013.01); A61K 2039/5254 (2013.01); C12N 2710/16621 (2013.01); C12N 2710/16634 (2013.01); C12N 2710/16643 (2013.01); C12N 2710/16651 (2013.01); C12N 2710/16662 (2013.01); C12N 2710/16671 (2013.01); C12N 2830/002 (2013.01)

(58) Field of Classification Search
CPC .............. A61K 39/245; A61K 39/0011; A61K 2039/5254; A61K 2039/5256; A61K 2039/70; A61K 39/02; A61P 31/12; C12N 15/86; C12N 2710/16621; C12N 2710/16634; C12N 2710/16643; C12N 2710/16651; C12N 2710/16662; C12N 2710/16671; C12N 2830/002; C12N 7/00
See application file for complete search history.

(56) References Cited

U.S. PATENT DOCUMENTS

| | | | | |
|---|---|---|---|---|
| 5,728,379 A * | 3/1998 | Martuza | ................. | A61P 35/00 435/456 |
| 6,342,596 B1 * | 1/2002 | Voellmy | ................. | A61P 37/08 435/235.1 |
| 7,279,565 B2 * | 10/2007 | Voellmy | ............. | C07K 14/4705 435/235.1 |
| 7,906,312 B2 | 3/2011 | Voellmy | | |
| 8,722,867 B2 * | 5/2014 | Gruber | .................... | C12N 9/78 424/94.1 |
| 9,315,825 B2 * | 4/2016 | Wilson | ....................... | A61P 7/04 |
| 10,478,486 B2 * | 11/2019 | Voellmy | ................. | A61P 37/04 |
| 11,497,806 B2 * | 11/2022 | Voellmy | ................. | A61P 31/22 |
| 11,505,782 B2 * | 11/2022 | Draganov | .......... | G01N 33/5005 |
| 2002/0187163 A1 * | 12/2002 | Johnson | ............... | A61K 38/162 424/229.1 |
| 2005/0130306 A1 * | 6/2005 | Voellmy | ................. | C12N 15/86 435/235.1 |
| 2013/0212722 A1 * | 8/2013 | West | ................. | A01K 67/0275 800/15 |

(Continued)

FOREIGN PATENT DOCUMENTS

| | | | | |
|---|---|---|---|---|
| WO | WO 96/39841 | 12/1996 | | |
| WO | WO-2016030392 A1 * | 3/2016 | ............. | A61K 39/12 |

OTHER PUBLICATIONS

Bloom DC, Tran RK, Feller J, Voellmy R. Immunization by replication-competent controlled herpesvirus vectors. Preprint Apr. 11, 2018. bioRxiv 299230; doi: https://doi.org/10.1101/299230. Now published in Journal of Virology doi: 10.1128/jvi.00616-18. (Year: 2018).*

(Continued)

*Primary Examiner* — Rachel B Gill
(74) *Attorney, Agent, or Firm* — SALIWANCHIK, LLOYD & EISENSCHENK

(57) ABSTRACT

The present disclosure relates to replication-competent controlled herpesviruses whose transient replication in a desired inoculation site region of a subject can be activated by the delivery of an appropriate heat dose to the inoculation site region. In related recombinant viruses, activation requires delivery of a heat dose in the presence in the inoculation site region of an effective concentration of a small-molecule regulator. The viruses are further engineered to be capable of replicating efficiently in the desired inoculation site region but essentially not in nerve ganglia and other nerve cells.

12 Claims, 3 Drawing Sheets

Specification includes a Sequence Listing.

(56) References Cited

U.S. PATENT DOCUMENTS

| | | | |
|---|---|---|---|
| 2016/0153000 A1* | 6/2016 | Glorioso | C12N 7/00 |
| | | | 435/456 |
| 2020/0009268 A1* | 1/2020 | Scholz | C12N 15/85 |
| 2020/0165302 A1* | 5/2020 | Vandermeulen | A61P 31/00 |
| 2021/0401968 A1* | 12/2021 | Voellmy | A61K 39/12 |
| 2022/0213508 A1* | 7/2022 | Glorioso, III | A61P 21/00 |

OTHER PUBLICATIONS

Vandermeulen G, Richiardi H, Escriou V, Ni J, Fournier P, Schirrmacher V, Scherman D, Préat V. Skin-specific promoters for genetic immunisation by DNA electroporation. Vaccine. Jul. 9, 2009;27(32):4272-7. Epub May 29, 2009. (Year: 2009).*

Miyagawa Y, Marino P, Verlengia G, Uchida H, Goins WF, Yokota S, Geller DA, Yoshida O, Mester J, Cohen JB, Glorioso JC. Herpes simplex viral-vector design for efficient transduction of nonneuronal cells without cytotoxicity. Proc Natl Acad Sci U S A. Mar. 31, 20151;112(13):E1632-41. Epub Mar. 16, 2015.; (Year: 2015).*

Miyatake S, Iyer A, Martuza RL, Rabkin SD. Transcriptional targeting of herpes simplex virus for cell-specific replication. J Virol. Jul. 1997;71(7):5124-32. (Year: 1997).*

Genetic Engineering and Biotechnology News. "Vical Halts Development of HSV-2 Vaccine after Phase II Failure." https://www.genengnews.com/news/vical-halts-development-of-hsv-2-vaccine-after-phase-ii-failure/. Jun. 11, 2018. (Year: 2018).*

Mahant AM, Guerguis S, Blevins TP, Cheshenko N, Gao W, Anastos K, Belshe RB, Herold BC. Failure of Herpes Simplex Virus Glycoprotein D Antibodies to Elicit Antibody-Dependent Cell-Mediated Cytotoxicity: Implications for Future Vaccines. J Infect Dis. Nov. 1, 2022;226(9):1489-1498. (Year: 2022).*

Harbecke R, Oxman MN, Selke S, Ashbaugh ME, Lan KF, Koelle DM, Wald A. Prior Herpes Simplex Virus Infection and the Risk of Herpes Zoster. J Infect Dis. Jul. 6, 2023:jiad259. Epub ahead of print. (Year: 2023).*

Sloutskin A, Yee MB, Kinchington PR, Goldstein RS. Varicella-zoster virus and herpes simplex virus 1 can infect and replicate in the same neurons whether co- or superinfected. J Virol. May 2014;88(9):5079-86. Epub Feb. 26, 2014. (Year: 2014).*

Jing L, Laing KJ, Dong L, Russell RM, Barlow RS, Haas JG, Ramchandani MS, Johnston C, Buus S, Redwood AJ, White KD, Mallal SA, Phillips EJ, Posavad CM, Wald A, Koelle DM. Extensive CD4 and CD8 T Cell Cross-Reactivity between Alphaherpesviruses. J Immunol. Mar. 1, 2016;196(5):2205-2218. Epub Jan. 25, 2016. (Year: 2016).*

Voellmy R, Bloom DC, Vilaboa N. A novel approach for addressing diseases not yielding to effective vaccination? Immunization by replication-competent controlled virus. Expert Rev Vaccines. May 2015;14(5):637-51. Epub Feb. 12, 2015.*

Hu C, Yang J, Qi Z, Wu H, Wang B, Zou F, Mei H, Liu J, Wang W, Liu Q. Heat shock proteins: Biological functions, pathological roles, and therapeutic opportunities. MedComm (2020). Aug. 2, 2022;3(3):e161. (Year: 2022).*

Noonan EJ, Place RF, Giardina C, Hightower LE. Hsp70B' regulation and function. Cell Stress Chaperones. 2007 Winter;12(4):393-402. (Year: 2007).*

Voon DC, Subrata LS, Baltic S, Leu MP, Whiteway JM, Wong A, Knight SA, Christiansen FT, Daly JM. Use of mRNA- and protein-destabilizing elements to develop a highly responsive reporter system. Nucleic Acids Res. Feb. 16, 2005;33(3):e27. (Year: 2005).*

Kennedy PG, Rovnak J, Badani H, Cohrs Rj. A comparison of herpes simplex virus type 1 and varicella-zoster virus latency and reactivation. J Gen Virol. Jul. 2015;96(Pt 7):1581-602. doi: 10.1099/vir.0.000128. Epub Mar. 20, 2015. (Year: 2015).*

Baines JD, Pellett PE. Genetic comparison of human alphaherpesvirus genomes. In: Arvin A, Campadelli-Fiume G, Mocarski E, et al., editors. Human Herpesviruses: Biology, Therapy, and Immunoprophylaxis. Cambridge: Cambridge University Press; 2007. Chapter 5. https://www.ncbi.nlm.nih.gov/books/NBK47393/ (Year: 2007).*

Voellmy R, Bloom DC, Vilaboa N. Herpes Simplex Viruses Whose Replication Can Be Deliberately Controlled as Candidate Vaccines. Vaccines (Basel). May 18, 2020;8(2):230. (Year: 2020).*

Nishiyama Y. Herpesvirus genes: molecular basis of viral replication and pathogenicity. Nagoya J Med Sci. Dec. 1996;59(3-4):107-19. (Year: 1996).*

Dogrammatzis C, Waisner H, Kalamvoki M. "Non-Essential" Proteins of HSV-1 with Essential Roles In Vivo: A Comprehensive Review. Viruses. Dec. 23, 2020;13(1):17. (Year: 2020).*

Nishiyama Y. Herpes simplex virus gene products: the accessories reflect her lifestyle well. Rev Med Virol. Jan.-Feb. 2004;14(1):33-46. (Year: 2004).*

Lilley CE, Groutsi F, Han Z, Palmer JA, Anderson PN, Latchman DS, Coffin RS. Multiple immediate-early gene-deficient herpes simplex virus vectors allowing efficient gene delivery to neurons in culture and widespread gene delivery to the central nervous system in vivo. J Virol. May 2001;75(9):4343-56. (Year: 2001).*

Kennedy PG. Potential use of herpes simplex virus (HSV) vectors for gene therapy of neurological disorders. Brain. Jul. 1997;120 (Pt 7):1245-59. (Year: 1997).*

Epstein AL. HSV-1-derived amplicon vectors: recent technological improvements and remaining difficulties—a review. Mem Inst Oswaldo Cruz. May 2009;104(3):399-410. (Year: 2009).*

Smith SN, Paige C, Velazquez KT, Smith TP, Raja SN, Wilson SP, Sweitzer SM. Injury-specific promoters enhance herpes simplex virus-mediated gene therapy for treating neuropathic pain in rodents. J Pain. Mar. 2015;16(3):283-90. Epub Jan. 7, 2015. (Year: 2015).*

Pawlik TM, Nakamura H, Mullen JT, Kasuya H, Yoon SS, Chandrasekhar S, Chiocca EA, Tanabe KK. Prodrug bioactivation and oncolysis of diffuse liver metastases by a herpes simplex virus 1 mutant that expresses the CYP2B1 transgene. Cancer. Sep. 1, 2002;95(5):1171-81. (Year: 2002).*

Mullen JT, Kasuya H, Yoon SS, Carroll NM, Pawlik TM, Chandrasekhar S, Nakamura H, Donahue JM, Tanabe KK. Regulation of herpes simplex virus 1 replication using tumor-associated promoters. Ann Surg. Oct. 2002;236(4):502-12; discussion 512-3. (Year: 2002).*

Bloom, D.C., Tran, R.K., Feller, J., Voellmy, R. (2018) Immunization by replication-competent controlled herpesvirus vectors. J. Virol. 92(16): e00616-18.

Search report and opinion ISA (EPO) relating to priority application EP18207121.7.

Vilaboa, N. et al. "A Broad Influenza Vaccine Based on a Heat-Activated, Tissue-Restricted Replication-Competent Herpesvirus" Vaccines, Jun. 23, 2024, pp. 1-26, vol. 12.

* cited by examiner

Figure 1

Promoter and RNA leader sequences of the mouse KRT1 gene (-1200 to +200)

AGGATCTGACACGCTGTCCTTAGCTAGGCACCGTCAGTTACACCCCAGGTGGACTTAACC
ACCCATGAAGATGTGGGGGAGCTTTTCAGACCTCATGCCTCACCTTTCTCATTTACAAAT
GGGTAGACTGATACTATTCTCAAACTTCTATGAACATTCACTTACAACATATAAGCCACA
AAACACTTTCAGGTACATAACCAATTCCTGACTGGCTTTAGCCCCTTCCCGCATCCTGAC
CCCTGCCATCATAGTCGCCACCAACTCTTAGAAACACCGCAAGCTTCTCAGGTCAGGTTT
TCCAGATTTTCATAACTGCTTCCTCTTCCAAACCCACACTTATCTCTTCTATGGTTCAGC
GTGAGGTGAGGTTTGAATCTGTCATGCCTCAACTACCCCACTCCGCTTTGCCACACGTGC
CAGTGCCGACGTACCCCACCAGTCCATGCACTTTTTATAATGGCATTTGCAAGCTGCCTA
TTTTCAACTGCTAGCCTCTTATGCCTGCTGTTCCTCATTTGAAGAGGAACAAGCAGGAAG
CCCAGGAAAGTATACGCCATTCCCTTGGTGCTTCTAGCCCACCCACCCCTCCATCCTGCT
TAGTGACAGCTGCCCCTTCTTTAATCGATCAGCGAGGTGCATTTGAAAACTTATTCTAGA
AAACATTGGATTTTTTTCCTTTGCTCTGTGTCAGGAGATGTGATTTGGTGAACCCTGGG
GTTTGAAGGGACAAGTCTCAGAAATGGATGAGGAAAGGAAATCCCTCCTTTAGGGATTCA
AGCTCGACTGAGCACACCTGTTACTCAAGGAACCGACAATACCCTAGTGAGTGTGTGGGC
ATGTGAGCCCATGAGCTGGGGATTACAGCTCGACAGTGCTGGGGGTTACGAAATCCTATC
AAGAGTCACCAAGAAGTCAGTGTGGGGTCCTACTTTCTCAAAGTCACAGACACTCTGAA
GAGAGATCCTGTCTGATAAAGAAAGTGATTACCACACGAGCCATTCTTGTCTGCACAGCA
ATTCTGAGAGCCCATCCTGGGAGCTAGGTGTGTAGTGTTTATCGTATTGTTGAGGCTCGT
AAAAATCTTGTATGGCTGCAGGCGAGCCAAACCCTTTGCAGGCTTTGCATCTCCGGCTGA
CTCTGAGGACCAAGCCCAATTTCTTCTCAGTATATAAGGGCACGGCACTGGGCTCAAGGC
AGAGGAGTTCTCAGCTCCTTCCATCTCTTGTCTTTGCTCTCACCTCTCTCTAAGGCATCA
TGAGTCTACAGTGTAGCTCCAGGTCCCTGTGCCGCGGTGGCGGTGGCAGCAGGAACTTCA
GCTCAGGCTCTGCTGGCCTAGTCAGCTTCCAGCGCAGATCCACCAGCAGCTCTATGCGCC
GCAGCGGTGGAGGTGGTGGT

Figure 2

Promoter and RNA leader sequences of the mouse KRT77 gene (-1200 to +200)

```
AAAAAGAACATTAGGAGAAAATGTTCCACAATCTGCAAGAGAGCGATTTAAATTCCCCCA
TGTTGAGCTGAGCAGCAACCCTTTGCAACATTGTATAATGATTCTTCTGGACCGGCTATG
CTTTCTTCTGGTTTTAAACAATTGTGTCCATGTGGGCAAATCATTGATCATTATTTTCTG
AAGCTGGGAATTTATTCTTTCTCTTCATGATCACAAGATTTATTAGTGCGTTTTGGTGCA
GTTGGGTGTGAATATGGGAATGAAGAGAACGAACATGCACTAGCTATTTGTGTCCAAGTG
CAAACACACACTTCTGTTGGACAACACTTGTAGACTCTCATGAACTTCACATTACGTCTT
CTGCTGGGACAGCCCTTTCTTCTCAGAGAGTGCGCATGAGCCAAGGTTCCTTTCCTACTA
CTCCCTGATAAGTACAGAAGGTGAGAGTAATGCTTTAAGAACTCACTATTATTGTTACTG
TCTCTGCCAGGAGAAAAATTTTATGCTGACCAAATAATAATACTAAATCCAAATTAAGGC
TTGTGTTTCACATACCTGTGGTCTTTATGTATTTCTTAAAAGATAGCTACTTTTTCTTTT
TACAAAAATATTGTCGGTGCCAGTTTAGAAATATTAGAATAGAAGAAGACATATGGGAGT
AGTTCTCCTCTGAGTCTAGGAGACATTCATACTGGGAGATGCTCACAGATATTTTGTTCA
CACACATGCATGCACACACCAAACAAACAAACAAACAAACAAAAAACCACAAACAAAAA
ATGGATTTTATGTACGAGGACAGCCTTGTTACAGCAAGTGTCTCCACTCTCATCCAAGCT
GTGGCCCCAAGGTCACTAGACACTTCATAGTTTTATCCTAGATCTCTCTGGCACACCCCA
AAACAAACAACTCCATGCTGCTTCTTAGGAAAAGATCAATTTGAGATTTAAGGAGAAACA
CTACAGGAGTTTCCAACACTGAGATCCTGAGAGATTGCTATCCTTTGGTCTCTCCGTAGT
AAGAGATGAATGATAAATGATCAAGTTGGGGGAGTTTGTCTGCAATGCCATTTCAGCAAC
ACATAGGTATGAGGCTTGTAAGCAGATGCTACTGGCAGGCAAATACTCCCCTCCCAGGGT
TCGGAAAGTTTCCAGCCCAGCAGGTGTGTGTATATATAGGGACTGAGCCAGATCCTTTCC
AAGAGAGTCGCAGCTCCCTCAGTCCCTGCTCTCTGCCTGCTTTCAGCTGAGTCCTTGCTA
CCAGTGCTTCTGGTTGCCCTAGCAACCATGAGCCGCCAGTTTAGTTCTCAGTCTGCATTT
AGCTCGAGGAGCAGGAGGGCCTATAGCTCCAGGTCTTCATCAGGCTTTGGAGGTGGGAGA
CAGGCTCTGGTGTCTGTGAG
```

Figure 3

Nucleotide sequence of the human HSF1-coding region and flanking sequences

```
CGNTGCTCGTTACTTAGCTTGTTACCATGGATCTGCCCGTGGGCCCCGGCGCGGCGG
GGCCCAGCAACGTCCCGGCCTTCCTGACCAAGCTGTGGACCCTCGTGAGCGACCCGG
ACACCGACGCGCTCATCTGCTGGAGCCCGAGCGGGAACAGCTTCCACGTGTTCGACC
AGGGCCAGTTTGCCAAGGAGGTGCTGCCCAAGTACTTCAAGCACAACAACATGGCCA
GCTTCGTGCGGCAGCTCAACATGTATGGCTTCCGGAAAGTGGTCCACATCGAGCAGG
GCGGCCTGGTCAAGCCAGAGAGAGACGACACGGAGTTCCAGCACCCATGCTTCCTGC
GTGGCCAGGAGCAGCTCCTTGAGAACATCAAGAGGAAAGTGACCAGTGTGTCCACCC
TGAAGAGTGAAGACATAAAGATCCGCCAGGACAGCGTCACCAAGCTGCTGACGGACG
TGCAGCTGATGAAGGGGAAGCAGGAGTGCATGGACTCCAAGCTCCTGGCCATGAAGC
ATGAGAATGAGGCTCTGTGGCGGGAGGTGGCCAGCCTTCGGCAGAAGCATGCCCAGA
ACAGAAAGTCGTCAACAAGCTCATTCAGTTCCTGATCTCACTGGTGCAGTCAAACCG
GATCCTGGGGGTGAAGAGAAAGATCCCCCTGATGCTGAACGACAGTGGCTCAGCACA
TTCCATGCCCAAGTATAGCCGGCAGTTCTCCCTGGAGCACGTCCACGGCTCGGGCCC
CTACTCGGCCCCCTCCCCAGCCTACAGCAGCTCCAGCCTCTACGCCCCTGATGCTGT
GGCCAGCTCTGGACCCATCATCTCCGACATCACCGAGCTGGCTCCTGCCAGCCCCAT
GGCCTCCCCCGGCGGGAGCATAGACGAGAGGCCCCTATCCAGCAGCCCCCTGGTGCG
TGTCAAGGAGGAGCCCCCCAGCCCGCCTCAGAGCCCCGGGTAGAGGAGGCGAGTCC
CGGGCGCCCATCTTCCGTGGACACCCTCTTGTCCCGACCGCCCTCATTGACTCCAT
CCTGCGGGAGAGTGAACCTGCCCCGCCTCCGTCACAGCCCTCACGGACGCCAGGGG
CCACACGGACACCGAGGGCCGGCCTCCCTCCCCCCGCCCACCTCCACCCCTGAAAA
GTGCCTCAGCGTAGCCTGCCTGGACAAGAATGAGCTCAGTGACCACTTGGATGCTAT
GGACTCCAACCTGGATAACCTGCAGACCATGCTGAGCAGCCACGGCTTCAGCGTGGA
CACCAGTGCCCTGCTGGACCTGTTCAGCCCCTCGGTGACCGTGCCCGACATGAGCCT
GCCTGACCTTGACAGCAGCCTGGCCAGTATCCAAGAGCTCCTGTCTCCCCAGGAGCT
CCCCAGGCCTCCCGAGGCAGAGAACAGCAGCCCGGATTCAGGGAAGCAGCTGGTGCA
CTACACAGCGCAGCCGCTGTTCCTGCTGGACCCCGGCTCCGTGGACACCGGGAGCAA
CGACCTGCCGGTGCTGTTTGAGCTGGGAGAGGGCTCCTACTTCTCCGAAGGGGACGG
CTTCGCCGAGGACCCCACCATCTCCCTGCTGACAGGCTCGGAGCCTCCCAAAGCCAA
GGACCCCACTGTCTCCTAGAGGCCCCGGAGGAGCTGGGCCAGCCGCCCACCCCCACC
CCCAGTGCAGGGCTGGTTTTGGGGAGGCAGGGCAGCCTCGCGGTTTTGGGCACTGGT
GGGTCGGCCGCCATAGCCCCAGTAGGACAAACGGGCTCGGGTCTGGGCAGCACCTCT
GGTCAGGAGGGTCACCCTGGCCTGCCAGTCTGCCTTCCCCCAACCCCGTGTCCTGTG
GTTTGGTTGGGGCTTCACAGCCACACCTGGACTGACCCTGCAGGTTGTTCATAGTCA
GAATTGTATTTTGGATTTTTACACAACTGTCCCGTTCCCCGCTCCACAGAGATACAC
AGATATATACACACAGTGGATGGACGGACAAGACAGGCAGAGATCTATAAACAGACA
GGCTTTAAAAAAAAAAAAAAAAAAAAAAAAAAAAAAAAAAACCC
```

REPLICATION-COMPETENT CONTROLLED ALPHA-HERPESVIRUS VECTORS AND USES THEREFORE

CROSS-REFERENCE TO RELATED APPLICATIONS

This application claims the benefit of European Patent Application No. 18207121.7, filed 19 Nov. 2018, which application is incorporated herein by reference in its entirety.

REFERENCE TO THE SEQUENCE LISTING

The present application is being filed along with a Sequence Listing in electronic format. The Sequence Listing is provided as a file entitled "VIR4PCT-ST25-replace.txt", created Feb. 7, 2023, which is 12,007 bytes in size. The information in the electronic format of the Sequence Listing is incorporated herein by reference in its entirety.

TECHNICAL FIELD

The present invention relates to certain replication-competent controlled alpha-herpesviruses and their utilization, including for immunization and cancer therapy.

BACKGROUND OF THE INVENTION

Replication-competent controlled viruses are viruses whose replication is under deliberate control. They are capable of transiently replicating upon activation but are essentially nonreplicating in the absence of activation. The present disclosure is concerned with certain replication-competent controlled viruses (abbreviated herein as RCCHVs for replication-competent controlled herpesviruses) having particular beneficial properties. These RCCHVs are derived from virulent viruses of the alpha-herpesvirus subfamily, in particular mammalian HSV-1, HSV-2 and vaccinia viruses. While the primary targets of the latter viruses are mucoepithelial cells, their tropism is much broader. The viruses have a lytic phase during symptomatic infection as well as a latent phase where they lie dormant in sensory and cranial nerve ganglia but remain susceptible to reactivation.

Replication-competent controlled viruses were described previously. For example, Chong et al. (2002) described a complementing pair of adenoviruses, of which one virus expressed a gene for a rapamycin-controlled heterologous transactivator and the other contained an E1A gene that had been brought under the control of a transactivator-responsive promoter (Mol Ther (2002) 5: 195-203). Other replication-competent controlled viruses and virus pairs were disclosed In U.S. Pat. Nos. 7,906,312 and 8,137,947, respectively. In the RCCHVs described by Bloom et al. (2015) (J Virol (2015) 89: 10668-10679), a small-molecule regulator-controlled heterologous transactivator was expressed under the control of a promoter cassette comprising a heat shock promoter and a transactivator-responsive promoter, and the resident promoters of one or more replication-essential genes were replaced by transactivator-responsive promoters.

RCCHVs may be employed as vaccines or vaccine vectors. As demonstrated in Bloom et al. (2018), the efficient replication of activated RCCHVs substantially enhanced immune responses to the vectors or to heterologous antigens expressed by the vectors when compared to unactivated vectors or control viruses, respectively ((J Virol (2018) 92: e00616-18); see also International Patent Application Publication WO2016/030392). RCCHVs may also be used in oncolytic or other therapies.

SUMMARY OF THE INVENTION

The present disclosure relates to replication-competent controlled alpha-herpesvirus-derived viruses (RCCHVs) whose replication can be transiently activated in certain infected nonneural cells but that cannot be so activated in infected sensory or other neural cells.

Subsequent to administration to a tissue region of the body of a mammalian subject (also referred to as the inoculation site region), a heat-controlled RCCHV of this disclosure is induced to replicate by a localized administration of an appropriate heat dose to the inoculation site region. Heat can be focused. Hence, the virus can be activated to replicate only in the inoculation site region, minimizing any pathological effects that are known to be associated with disseminated replication of the wildtype virus. Subsequent to its heat activation, the virus will replicate with a high efficiency in the heated region. This replication is transient and ends with the lysis of the infected cells in the heated region. Hence, virus replication is also limited in time/extent, further decreasing the possibility of untoward pathological effects. Over the ensuing weeks, the virus is cleared from the body of the mammalian subject, except from sensory and, depending on the virus administration site, cranial nerve ganglia where it survives in a latent form. Virus reactivation which may otherwise occur if the mammalian subject is exposed to a severe physiological stress (high fever) is prevented because a replication-essential gene of the RCCHV has been placed under the control of a tissue-selective promoter that is essentially inactive in nerve ganglia of the mammalian subject. In the case of a heat- and small-molecule regulator (SMR)-controlled RCCHV, replication in the inoculation site region of a mammalian subject is triggered by a localized heat treatment in the presence of an effective concentration of the appropriate SMR. The efficient but transient replication ends when the concentration of the SMR has fallen to an ineffective level in the inoculation site region (as a result of elimination by normal physiological processes) or when all infected (and heat-exposed) cells have been lysed (whichever occurs first). Thereafter, in the absence of a re-administration of a dose of the SMR that suffices to co-activate the virus, the subject is expected to be protected from reactivation. However, in the absence of the above-described protective mechanism, there is no reason for believing that reactivation could not occur upon re-administration of an effective concentration of the SMR at a time at which the mammalian subject is also experiencing a stress. An SMR will be susceptible to at least sporadic re-administration to certain subjects, if it has an approved pharmacological activity. This is more than a theoretical possibility as SMRs of choice preferably are well known molecules that are readily available, have been tested in human toxicological studies and, ideally, are approved for human use.

An RCCHV of the present disclosure is a recombinant herpesvirus that comprises a first heterologous promoter that is a heat shock promoter or nucleic acid sequence that functions as a heat shock promoter. The term "heterologous" is meant to indicate that the genetic element it relates to is not identical with any genetic element of the herpesvirus that serves as the backbone for the construction of the RCCHV. The first heterologous promoter is employed to control, directly or indirectly as is discussed below, the expression of a first replication-essential gene.

In a first embodiment, the first heterologous promoter is inserted in the genome of the backbone herpesvirus so as to replace the resident (viral) promoter of the first replication-essential viral gene. Hence, the first replication-essential gene is placed under the control of the first heterologous promoter.

In a second embodiment, the first heterologous promoter controls the expression of a gene for a heterologous transactivator, whereby a cassette comprising the first heterologous promoter and the functionally linked transactivator gene is inserted in a suitable intergenic region in the genome of the backbone herpesvirus. A transactivator-responsive promoter is inserted in the genome of the virus so as to replace the resident promoter of the first replication-essential viral gene. Hence, the first replication-essential gene is placed under the control of the transactivator. In a variation of the second embodiment, the first heterologous promoter is a nucleic acid sequence to functions as a heat shock promoter as well as a transactivator-responsive promoter. The transactivator can be any unregulated transactivator that begins mediating transcription from a transactivator-responsive promoter in a mammalian cell as soon it (the transactivator) is synthesized in the cell. Preferred is a transactivator that does not affect or only minimally affects host gene expression in a mammalian host. The transactivator can also be a regulated transactivator that is incapable of mediating transcription from a transactivator-responsive promoter in a mammalian cell prior to an activating interaction with an appropriate SMR. An RCCHV of the present disclosure that carries a gene for an SMR-activated transactivator is referred to as a heat- and SMR-controlled RCCHV, and an RCCHV that does not express a regulated transactivator is referred to as a heat-controlled RCCHV. In principle, the regulated transactivator can be any transactivator that can be activated by an SMR. Preferred is a transactivator that does not affect or only minimally affects host gene expression in a mammalian host and for which an SMR is available that has no undue toxicity in the mammalian subject to which RCCHVs are to be administered. As discussed further below, there are several transactivator/SMR combinations that may satisfy the latter requirements. Preferred is a regulated transactivator that contains a truncated ligand-binding domain from a progesterone receptor and is activated by a progesterone receptor antagonist (antiprogestin) or other molecule capable of interacting with the ligand-binding domain and of activating the transactivator. Typical for the class of antiprogestins that activate the latter transactivator are mifepristone and ulipristal. The most preferred transactivator is GLP65. Burcin et al. (1999) (Proc Natl Acad Sci USA (1999) 96: 355-60); Ye et al. (2002) (Meth Enzymol (2002) 346: 551-61).

An RCCHV of the present disclosure further comprises a second heterologous promoter that replaces the resident promoter of a second replication-essential viral gene. Hence, the second replication-essential viral gene has been placed under the control of the second heterologous promoter. The second heterologous promoter is a promoter that is known to be active in cells in the intended inoculation site region of a mammalian subject (i.e., the region to which the RCCHV is to be administered) but is known to be essentially inactive in the cells of the nerve ganglia of the mammalian subject. The terms "known to be active" and "known to be essentially inactive" refer to transcript levels of the gene that is naturally controlled by the chosen second heterologous promoter as published in professional databases, of which BioGPS is a preferred database (biogps.org). A suitable second heterologous promoter is a promoter of a mammalian gene whose transcript level in tissue regions that are intended for administration of an RCCHV (inoculation site regions) is at least about 50 times, more preferably at least about 100 times and most preferably at least about 500 times higher than in (cells of) nerve ganglia or other nerve tissue. In addition, the transcript level of the latter mammalian gene in nerve ganglia or other nerve tissue is less than about three times the median transcript level of all tissues examined. Preferably, it is close to or less than the median transcript level of all tissues examined. It is noted that a transcript level corresponding to the median transcript level of a gene that is expressed in a highly tissue-specific fashion corresponds to a level that is close to or at the limit of detection, and a transcript level of three times the median transcript level is still extremely low. Hence, the promoter of such a gene is "essentially inactive".

The primary targets of the alpha-herpesvirues that can serve as backbones for the construction of RCCHVs of the present disclosure are mucoepithelial cells. Hence, a preferred inoculation site region of an RCCHV of the present disclosure can be a cutaneous or subcutaneous region, or a mucosal membrane of a mammalian subject. A particularly preferred inoculation site region may be an epidermal region, preferably an epidermal region on an extremity of a mammalian subject. With these preferences, the databases may be mined for genes that are active in the epidermis (or the skin) but are essentially inactive in nerve ganglia, e.g., the dorsal root ganglia. Such a search will uncover, e.g., the keratin-1 gene as is discussed further below. The promoter of this gene may serve as a second heterologous promoter for an RCCHV that is intended for administration to a skin region of a mammalian subject.

An RCCHV of the present disclosure can be derived from a (wildtype) herpes simplex virus 1 (HSV-1), a herpes simplex virus 2 (HSV-2), or a varicella zoster virus (VZV).

In an RCCHV of the present disclosure that has been derived from an HSV-1 or HSV-2, the viral gene ICP47 may be deleted or rendered nonfunctional. The product of this gene binds to transporters associated with antigen processing (TAP), interfering with the presentation of antigens to MHC class I molecules and, consequently, with immune recognition by cytotoxic T-lymphocytes.

An RCCHV of the present disclosure can be engineered to carry in its genome an expressible gene (or parts thereof) from another pathogen, an expressible heterologous gene encoding an immune-modulatory polypeptide or an expressed heterologous gene encoding another polypeptide or any combination of one or more of such genes (or gene portions). The latter heterologous genes (i.e., genes not originally present in the wildtype virus from which the RCCHV was derived) can be placed under the control of any suitable promoter, including a constitutively active viral or non-viral promoter, the first heterologous promoter (directly or indirectly as discussed above) or the second heterologous promoter. The gene for another pathogen can be a gene encoding an influenza virus surface antigen or internal protein or parts thereof (representing selected polypeptide regions). It can also be a gene encoding a human immunodeficiency virus surface antigen or internal protein or parts thereof (representing selected polypeptide regions).

Also encompassed by the present disclosure are vaccine compositions or compositions for cancer therapy or genetic therapy which compositions comprise an effective amount of an RCCHV of the present disclosure and a pharmaceutically acceptable carrier or excipient. In the case of a heatand SMR-controlled RCCHV, a composition comprising an effective amount of an SMR that is capable of activating the heterologous transactivator can be co-administered with any one of the latter compositions or can be administered separately, including by a different route. For example, a vaccine composition can be administered topically to a region of the skin of a mammalian subject and an SMR-comprising composition may be administered systemically (e.g., per os). Alternatively, a vaccine composition or a composition for cancer therapy or for genetic therapy comprising an effective amount of an RCCHV and a pharmaceutically acceptable carrier or excipient may further comprise an effective amount of an SMR that is capable of activating the transactivator comprised in the RCCHV.

Also encompassed by the present disclosure are any uses of RCCHVs of the present disclosure (or of compositions comprising an effective amount of an RCCHV of the present disclosure and a pharmaceutically acceptable carrier or excipient), including for therapeutic or prophylactic vaccination of mammalian subjects. Vaccine uses can relate to vaccination against the virus from which the RCCHV was derived or, if a heterologous antigen of another pathogen is expressed from the RCCHV, against that other pathogen. Alternatively, uses may concern treatment, including oncolytic treatment, of a cancer (e.g., a melanoma) in a mammalian subject. Furthermore, they may relate to a genetic treatment of a condition or disease that responds to a protein expressed from a heterologous gene carried by the RCCHV.

BRIEF DESCRIPTION OF FIGURES

FIG. 1 presents a nucleotide sequence (SEQ ID NO: 1) for the promoter and RNA leader region of the mouse keratin 1 (KRT1) gene (retrieved from the Eukaryotic Promoter Database EPD (epd.epfl.ch)). The sequence includes 1200 nucleotide of 5' untranscribed sequence and the first 200 nucleotides of the transcript. The start of transcription site is bolded.

FIG. 2 presents a nucleotide sequence (SEQ ID NO: 2) for the promoter and RNA leader region of the mouse keratin 77 (KRT77) gene (retrieved from the Eukaryotic Promoter Database EPD (epd.epfl.ch)). The sequence includes 1200 nucleotide of 5' untranscribed sequence and the first 200 nucleotides of the transcript. The start of transcription site is bolded.

FIG. 3 shows the nucleotide sequence (SEQ ID NO: 27) of human HSF1 present in plasmid CMV-hHSF1. The protein-coding sequence is underlined.

DETAILED DESCRIPTION

Unless otherwise defined below or elsewhere in the present specification, all terms shall have their ordinary meaning in the relevant art.

"Replication of virus" or "virus/viral replication" are understood to mean multiplication of viral particles. Replication is often measured by determination of numbers of infectious virus, e.g., plaque-forming units of virus (pfu). However, replication can also be assessed by biochemical methods such as methods that determine amounts of viral DNA, e.g., by a real-time PCR procedure, levels of viral gene expression, e.g., by RT-PCR of gene transcripts, etc. However, it is understood that marginal increases in levels of viral DNA or viral gene transcripts or protein products may not translate in corresponding marginal increases in virus replication due to threshold effects.

A "small-molecule regulator" or "SMR" is understood to be a low molecular weight ligand of a transactivator used in connection with this invention. The SMR is capable of activating the transactivator. The SMR is typically, but not necessarily, smaller than about 1000 Dalton (1 kDa).

The term "transactivator" or "heterologous transactivator" is used herein to refer to a non-viral and, typically, engineered transcription factor that can positively affect transcription of a gene controlled by a transactivator-responsive promoter.

A "small-molecule regulator (SMR)-activated transactivator" or "heterologous small-molecule regulator (SMR)-activated transactivator" is a non-viral and, typically, engineered transcription factor that when activated by the appropriate small-molecule regulator (SMR) positively affects transcription of a gene controlled by a transactivator-responsive promoter.

A "transactivator-responsive promoter" is a promoter that contains one or more sequence elements that can be bound by a transactivator and that is essentially inactive prior to being bound by an active transcription factor.

"Activated" when used in connection with a transactivated gene means that the rate of expression of the gene is measurably greater after activation than before activation or, when used in connection with a controllable heterologous promoter means that the transcription-enhancing activity of the promoter is measurably greater after activation than before activation. When used in connection with a SMR-activated transactivator, "active" or "activated" refers to a transactivation-competent form of the transactivator. The transactivator is rendered transactivation-competent by the binding of the appropriate SMR.

Herein, a virus, whose genome includes a foreign (heterologous) non-viral or viral gene, is either referred to as a "virus" or a "viral vector".

A "replication-competent controlled virus" is a recombinant virus whose replicative ability is under deliberate control (i.e., whose replication can be triggered by a deliberate intervention). In such a virus, replication of at least one replication-essential viral gene is under the control of a gene switch that can be deliberately activated. A "replication-competent controlled herpesvirus", abbreviated as "RCCHV", is a replication-competent controlled virus that has been derived from a wildtype herpesvirus.

A "recombinant virus" or "recombinant" refers to a virus that has been altered by an experimenter.

A "heterologous promoter" is a promoter that, as a whole, does not naturally occur in the wildtype virus that serves as the backbone for the construction of a replication-competent controlled virus that contains the heterologous promoter. The possibility that such a heterologous promoter also contains elements of a viral promoter is encompassed by the term.

A "replication-essential gene" or a "gene required for efficient replication" is arbitrarily defined herein as a viral gene whose loss of function diminishes replication efficiency by a factor of ten or greater. Replication efficiency can be estimated, e.g., in a (single-step) growth experiment. For many viruses it is well known which genes are replication-essential genes. For herpesviruses see, e.g., Nishigawa (1996) (Nagoya L Med Sci (1996) 59: 107-19).

An "effective amount of a replication-competent controlled herpesvirus (RCCHV)" is an amount of virus that upon single or repeated administration to a subject followed by activation confers a therapeutic effect on the treated subject, at a reasonable benefit/risk ratio applicable to any medical treatment. When used in the context of prophylaxis or prevention, an "effective amount" of an RCCHV of the disclosure is meant to be an amount which, when administered (and thereafter activated) once or multiple times over the course of a prophylactic or preventative (e.g., vaccination) regime, confers a desired prophylactic effect on the treated subject. In general, what is an "effective amount" will vary depending on the route of administration as well as the possibility of co-usage with other agents. It will be understood, however, that the total or fractional dosage of compositions of the present disclosure comprising an RCCHV will be decided by the attending physician within the scope of sound medical judgment. The specific effective dose level for any particular subject may be adjusted based on a variety of factors including the disorder being treated and the severity of the disorder; the activity of the RCCHV employed; the specific composition employed; the age, body weight, general health, sex and diet of the patient; the time of administration, route of administration, and rate of elimination of the specific RCCHV employed; the duration of the treatment; drugs used in combination or contemporaneously with the RCCHV employed; and like factors well known in the medical arts. The latter factors will be considered in the context of therapeutic applications of replication-competent controlled viruses as well as in the context of prophylactic or preventative applications.

An "effective amount of a small-molecule regulator (SMR)" is an amount that when administered to a subject by a desired route is capable of co-activating a heat- and SMR-controlled RCCHV of the present disclosure with which the subject concurrently is, has been or will be inoculated to undergo at least one round of replication in the administration site region (also referred to as "inoculation site region").

A "subject" or a "mammalian subject" is a mammalian animal or a human person.

"Promoter of a heat shock gene", "heat shock gene promoter" and "heat shock promoter" are used synonymously. A "nucleic acid that acts as a heat shock promoter" can be a heat shock promoter or a nucleic acid that contains sequence elements of the type present in heat shock promoters which elements confer heat activation on a functionally linked gene.

A "heat shock gene" is defined herein as any gene, from any eukaryotic organism, whose activity is enhanced when the cell containing the gene is exposed to a temperature above its normal growth temperature. Typically, such genes are activated when the temperature to which the cell is normally exposed is raised by 3-10° C. Heat shock genes comprise genes for the "classical" heat shock proteins, i.e., HSP110, HSP90, HSP70, HSP60, HSP40, and HSP20-30. They also include other heat-inducible genes such as genes for MDR1, ubiquitin, FKBP52, heme oxidase and other proteins. The promoters of these genes, the "heat shock promoters", contain characteristic sequence elements referred to as heat shock elements (HSE) that consist of perfect or imperfect sequence modules of the type NGAAN or AGAAN, which modules are arranged in alternating orientations (Amin et al. (1988) (Mol Cell Biol (1988) 8: 3761-3769); Xiao and Lis (1988) (Science (1988) 239: 1139-1142); Fernandes et al. (1994) (Nucleic Acids Res (1994) 22: 167-173). These elements are highly conserved in all eukaryotic cells such that, e.g., a heat shock promoter from a fruit fly is functional and heat-regulated in a frog cell (Voellmy and Rungger (1982) (Proc Natl Acad Sci USA (1982) 79: 1776-1780). HSE sequences are binding sites for heat shock transcription factors (HSFs; reviewed in Wu (1995) (Annu Rev Cell Dev Biol (1995) 11: 441-469). The factor primarily responsible for activation of heat shock genes in vertebrate cells exposed to heat or a proteotoxic stress is heat shock transcription factor 1 (abbreviated as "HSF1") (Baler et al. (1993) (Mol Cell Biol (1993) 13: 2486-2496); McMillan et al. (1998) (J Biol Chem (1998) 273: 7523-7528). Preferred promoters for use in RCCHVs discussed herein are those of inducible HSP70 genes. A particularly preferred heat shock promoter is the promoter of the human HSP70B gene (Voellmy et al. (1985) (Proc Natl Acad Sci USA (1985) 82: 4949-4953).

"Vaccine" typically refers to compositions comprising microorganisms that are killed, replication-defective or otherwise attenuated. Herein, the term is expanded to also include compositions comprising RCCHVs that can induce an immune response in the subject to which they are administered.

Current thought appears to be that in order to be effective or more effective, respectfully, improved vaccine candidates for preventing or treating diseases such as herpes, HIV, tuberculosis or influenza need to elicit a balanced immune response that also includes a powerful effector T cell response. The present invention relates to RCCHVs that, upon activation, replicate with efficiencies that approach those of the respective wild type viruses. It is hypothesized that these recombinant viruses and any heterologous protein they express will be potent immunogens that elicit balanced immune responses.

To obtain an RCCHV of the present disclosure, a wild type HSV-1, HSV-2 or varicella zoster virus (VZV) is genetically altered by placing at least one replication-essential viral gene under the control of a gene switch that has a broad dynamic range, i.e., that essentially functions as an on/off switch. The gene switch can be a highly heat-inducible heat shock promoter or a nucleic acid sequence that functions as such a heat shock promoter (the promoter also being referred to herein as "first heterologous promoter"). Alternatively, it can be a highly heat-inducible heat shock promoter (or nucleic acid sequence that functions as such a heat shock promoter) that drives the expression of a gene for a heterologous transactivator, and the heterologous transactivator controls the expression of the replication-essential gene that is functionally linked to a transactivator-responsive promoter. As heat shock promoters can only be transiently activated, it may be advantageous to include an element that permits autoactivated synthesis of the transactivator. Hence, the transactivator gene may be controlled by a nucleic acid sequence that acts both as a heat shock promoter and as a transactivator-responsive promoter. Such a nucleic acid sequence is present in several of the exemplified RCCHVs and is specifically discussed in Example 2 that relates to the construction of HSV-GS1/3. See also FIG. 3 in Vilaboa et al. (2005) (Mol Ther (2005) 12: 290-298).

Any transactivator may be employed as long as it is transcriptionally competent when synthesized in a mammalian cell (i.e., is constitutively active) and comprises a DNA-binding domain that specifically binds to a DNA sequence element that is present in a transactivator-responsive promoter. Preferred is a transactivator that only minimally affects the expression of the resident genes in cells of a subject that are targeted by the RCCHV, i.e., that has no undue toxicity in these cells. Advantageously, the transactivator is an SMR-activated transactivator that is active in the presence of the SMR but is essentially inactive in its absence. To construct an RCCHV that relies on a highly heat-inducible heat shock promoter (or nucleic acid sequence that functions as such a heat shock promoter) as the gene switch, the resident promoter of at least one replication-essential gene in a wildtype herpesvirus is replaced with the latter heat shock promoter. To construct an RCCHV in which one or more replication-essential genes are controlled by a transactivator that is expressed from a heat shock promoter-driven gene, a wildtype herpesvirus is modified to contain the expressible gene for the transactivator in a location in the viral genome in which an insertion of such a gene does not interfere with virus function, in particular with replication efficiency. The U L43/44 and UL37/38 intergenic regions of HSV-1 are such locations. The promoters of the one or more replication-essential genes are replaced by transactivator-responsive promoters. The resulting recombinant viruses are referred to as heat-controlled or, when co-activated by an SMR, as heat- and SMR-controlled RCCHVs.

Wildtype HSV-1, HSV-2 or VZV are known to preferentially target mucoepithelial cells and to establish latency in cells of nerve ganglia, e.g., in cells of the dorsal root ganglia. The preferred RCCHVs of the present disclosure are engineered to replicate efficiently in mucoepithelial cells (and derived cells), e.g., epidermal cells of the skin, but, to prevent reactivation from latency, to not (or only minimally) replicate in cells of nerve ganglia. This is achieved by the use of an appropriate tissue- or cell type-specific or restricted (heterologous) promoter for controlling the expression of a further replication-essential gene. Hence, the construction of an RCCHV of the present disclosure involves replacement in the above-described heat-controlled or heat- and SM R-controlled RCCHV of the resident promoter of the further replication-essential gene with such a tissue- or cell type-specific or restricted (heterologous) promoter. It is understood that an RCCHV of the present disclosure can also be constructed by first replacing in a wildtype herpesvirus the promoter of a replication-essential gene with a tissue- or cell type-specific promoter and subsequently placing at least one further replication-essential gene under heat or heat and SMR control.

A tissue- or cell type-specific or restricted promoter that is appropriate for the intended use in an RCCHV of the present disclosure can be identified by mining available databases and other scientific literature (see, e.g., the BioGPS database or the article of Su et al. (2002) (Proc Natl Acad Sci USA (2002) 99: 4465-4470).

For an RCCHV of the present disclosure that is to be used as a vaccine or a vaccine vector and is to be administered to a region of the skin of a human subject, a promoter that is highly active in all epidermal layers of the human skin but not (or only minimally) in cells of nerve ganglia may be selected for driving the expression of one or more replication-essential viral genes. A particular promoter that may be employed is the human keratin 1 (KRT1) promoter. Edqvist et al. (2015) (J Histochem Cytochem (2015) 63: 129-41). Inspection of the BioGPS database (biogps.org) reveals that this promoter is essentially only expressed in skin (and other epithelia as discussed below). No expression is evident in nerve ganglia (Table 1). Another useful promoter is that of the human KRT10 gene. Transcript levels are far higher in the skin than in any other tissue/organ. Essentially no expression occurs in nerve ganglia. For an RCCHV vaccine to be administered to the skin of a murine subject, a suitable promoter may be that of the mouse KRT77 gene. The latter gene is highly active in the mouse epidermis but not in any other adult tissue. Essentially no expression occurs in the dorsal root ganglia. Other useful promoters may by the mouse KRT1 and KRT10 promoters for which essentially no activity has been demonstrated in nerve ganglia. That they are also active in the stomach may not significantly detract from their usefulness in vaccine applications. The nucleotide sequences of the latter promoters can be found in the Eukaryotic Promoter Database (epd.epfl.ch) and elsewhere.

For an RCCHV-based human vaccine directed against genital herpes or other sexually transmitted diseases that is to be administered to the vaginal mucosal epithelium with the intention of inducing resident immunity, reference is made to Borgdorff et al. (2016) (Mucosal Immunol (2016) 9: 621-33). The latter publication reports that the KRT1, KRT4, KRT5, KRT6A, KRT10 and KRT13 genes are abundantly expressed in the epithelial layer of the vagina. Preferred promoters for use in RCCHVs suitable for the latter applications are those of the KRT1, KRT4 and KRT13 genes that are most selectively active and appear to have essentially no activity in nerve ganglia.

TABLE 1

Expression of KRT genes

| Gene | ID | Rel. transcript level in skin | Rel. transcript level in dorsal root ganglia | Rel. transcript level over all tissues-median |
|---|---|---|---|---|
| Mouse KRT1 | 16678 | 13452 (epidermis) | 4.7 | 4.6 |
| Human KRT1 | 3848 | 6713 | 2.9 | 3.9 |
| Mouse KRT77 | 406220 | 37271 | 4.6 | 4.6 |
| Mouse KRT10 | 16661 | 92700 (epidermis) | 158 | 124 |
| Human KRT10 | 3858 | 5939 | 15 | 93 |

Data from the BioGPS database

For an RCCHV-based oncolytic therapy of human melanoma, in particular primary melanoma, a suitable promoter may be that of the human MLANA gene or, possibly, that of the human TYR gene. Weinstein et al. (2014) (J Clin Aesthet Dermatol (2014) 7: 13-24). Both promoters typically have elevated activity in skin melanomas (Human Protein Atlas; proteinatlas.org) but only minimal activity in nerve ganglia.

Tissue- or cell type-specific promoters for controlling the expression of one or more replication-essential genes in an RCCHV of the present disclosure, including the promoters specifically disclosed above, are selected because they are active in the intended target cells but essentially inactive in cells of nerve ganglia, and their use in the herpesvirus recombinants is expected to preclude or minimize the possibility of reactivation of the viruses from latency. It appears improbable that, when using such selective promoters, an unacceptable level of replication is detected in neural cells (which is a level that enables detectable reactivation from latency in a subject). However, if this occurs, it is likely that the promoter concerned is also excessively active in the target cells, i.e., that highly efficient (wildtype-like) replication could be had at a considerably lower level of promoter activity. Hence, to reduce such undue viral replication in neural cells, it may be indicated to generally reduce the level of expression of the replication-essential gene(s) controlled by the promoter. Various engineering approaches to achieve this goal are known in the art. For example, protein-destabilizing elements could be introduced into the replication-essential protein, e.g., near the carboxy terminus of the protein. Well known sequence elements of this type are the so-called PEST sequences that are thought to function as proteolytic signals. Rechsteiner and Rogers (1996) (Trends Biochem Sci (1996) 21: 267-71). These sequences contain regions enriched in proline (P), glutamate (E), serine (S) and threonine (T). PEST sequences are hydrophilic stretches of at least 12 amino acids in length, with the entire region flanked by lysine (K), arginine (R) or histidine (H), but not interrupted by positively charged residues. RNA-destabilizing elements, AU-rich elements (ARE), may be added to the 3'UTR sequence of the replication-essential gene. Such elements were described in Zubiaga et al. (1995) (Mol Cell Biol (1995) 15: 2219-30). See also Matoulkova et al. (2012) RNA Biol 9: 563-76. RNA- and protein-destabilizing elements have also been used in combination to dramatically reduce protein levels. Voon et al. (2005) Nucleic Acids Res 33 (3): e27. Other approaches are aimed at reducing translation efficiency. The introduction of highly stable secondary structure (hairpins) near the 5' end of the gene can dramatically reduce translation efficiency as shown by Babendure et al. (2006) (RNA (2006) 12: 851-61). Hence, such secondary structure elements could be introduced into the replication-essential gene to reduce its expression.

The following description illustrates how an RCCHV of the present disclosure may be employed. The narrative focuses on vaccine uses. How the RCCHVs could be used for other therapeutic or prophylactic purposes should also become readily apparent from this description.

In an exemplary vaccine application, a composition comprising an effective amount of a heat-controlled or a heat- and SMR-controlled RCCHV of the present disclosure and, in the case of a heat- and SMR-controlled RCCHV, an effective amount of an SMR is administered to a subject intradermally or subcutaneously. Shortly after administration, a heating patch is activated and applied to the inoculation site region by either the subject or the physician. Heating at about 43.5-45.5° C. (temperature of the patch surface in contact with the skin) will be for a period of about 10-60 min. The latter heat treatment will trigger one cycle of virus replication. If another round of replication is desired, another activated patch is applied to the inoculation site region at an appropriate later time. If an immunization procedure employing a heat- and SMR-controlled RCCHV involves sequential heat treatments, SMR may also need to be administered sequentially. Alternatively, a slow release formulation may be utilized that assures the presence of an effective concentration of the SMR in the inoculation site region over the period during which viral replication is desired.

More generally, a body region to which an RCCHV of the present disclosure is administered, i.e., the inoculation site region, may be heated by any suitable method. Heat may be delivered or produced in the target region by different means including direct contact with a heated surface or a heated liquid, ultrasound, infrared radiation, or microwave or radiofrequency radiation. As proposed in the above specific example, a practical and inexpensive solution may be offered by heating patches (or similar devices of other shapes, e.g., cylinders or cones, for heating mucosal surfaces of the nose, etc.) containing a supercooled liquid that can be triggered by mechanical disturbance to crystallize, releasing heat at the melting temperature of the chemical used. A useful chemical may be sodium thiosulfate pentahydrate that has a melting temperature of about 48° C. U.S. Pat. Nos. 3,951,127, 4,379,448, and 4,460,546. The technology is readily available and is already being used in a number of health care products. That such heating patches are capable of activating heat shock promoters in all human skin layers has been verified experimentally. Voellmy et al. (2018) Cell Stress Chaperones 23(4): 455-466.

An "activating heat dose" is a heat dose that causes a transient activation of heat shock transcription factor 1 (HSF1) in cells within the inoculation site region. Activation of HSF1 is evidenced by a detectably increased level of RNA transcripts of a heat-inducible heat shock gene over the level present in cells not exposed to the heat dose. Alternatively, it may be evidenced as a detectably increased amount of the protein product of such a heat shock gene. Moreover, an activating heat dose may be evidenced by the occurrence of replication of a heat-controlled RCCHV, in the presence of an effective concentration of an appropriate small-molecule regulator in the case of a heat- and SMR-controlled RCCHV.

An activating heat dose can be delivered to the target region at a temperature between about 41° C. and about 47° C. for a period of between about 1 min and about 180 min. It is noted that heat dose is a function of both temperature and time of exposure. Hence, similar heat doses can be achieved by a combination of an exposure temperature at the lower end of the temperature range and an exposure time at the upper end of the time range, or an exposure temperature at the higher end of the temperature range and an exposure time at the lower end of the time range. Preferably, heat exposure will be at a temperature between about 42° C. and about 46° C. for a duration of between about 5 min and about 150 min. Most preferably, heat treatment is administered at a temperature between about 43.5° C. and about 45.5° C. for a duration of between about 10 min and about 60 min. It is noted that it appears feasible to deliver an activating heat dose within a much shorter time, i.e., within seconds or even in the sub-second range, by intense irradiation of the target region. Tolson and Roberts (2005) (Methods (2005) 35:149-157); Sajjadi et al. (2013) (Med Eng Phys (2013) 35:1406-1414).

Concerning heat- and SMR-controlled RCCHVs of the present disclosure, an SMR should satisfy a number of criteria. Most important will be that the substance is safe; adverse effects should occur at most at an extremely low rate and should be generally of a mild nature. Ideally, an SMR would belong to a chemical group that is not used in human therapy. However, before any substance not otherwise developed for human therapy could be used as an SMR in a medical application of an RCCHV, it would have to undergo extensive preclinical and clinical testing. It may be more efficacious to select a known and well-characterized drug substance that is not otherwise administered to the specific population targeted for treatment or immunization using an RCCHV. Alternatively, a known drug substance that will not need to be administered to subjects within at least the first several weeks after RCCHV-mediated treatment or immunization may be selected as an SMR. Thus, the potential low-level risk of disseminated replication of the RCCHV would be further reduced by the avoidance of administration of the drug substance during the period during which the RCCHV is systemically present. Subsequent, ideally sporadic, use of the drug substance under medical supervision will ensure that any significant inadvertent replication of an RCCHV would be rapidly diagnosed and antiviral measures could be taken without delay. In examples described herein, the SMR is a progesterone receptor (PR) antagonist or antiprogestin, e.g., mifepristone or ulipristal. Mifepristone and ulipristal fulfill the latter requirement of not typically needing to be administered shortly after virus administration. Mifepristone and ulipristal have excellent human safety records.

An effective concentration of an SMR in the inoculation site region is a concentration that enables replication (at least one round) of an RCCHV in infected cells of that region. What an effective concentration is depends on the affinity of the SMR for its target transactivator. How such effective concentration is achieved and for how long it is maintained also depends on the pharmacokinetics of the particular SMR, which in turn depends on the route or site of administration of the SMR, the metabolism and route of elimination of the SMR, the subject to which the SMR is administered, i.e., the type of subject (human or other mammal), its age, condition, weight, etc. It further depends on the type of composition administered, i.e., whether the composition permits an immediate release or a slow release of the regulator. For a number of well-characterized SMR-transactivator systems, effective concentrations in certain experimental subjects have been estimated and are available from the literature. This applies to systems based on progesterone receptor, ecdysone receptors, estrogen receptors, and tetracycline repressor as well as to dimerizer systems, i.e., transactivators activated by rapamycin or analogs (including non-immunosuppressive analogs), or FK506 or analogs. For example, an effective concentration of mifepristone in rats can be reached by i.p. (intraperitoneal) administration of 5 μg mifepristone per kg body weight (5 μg/kg). Amounts would have to be approximately doubled (to about 10 μg/kg), if the SMR is administered orally. Wang, Y. et al. (1994) Proc Natl Acad Sci USA 91: 8180-84. Amounts of an SMR that, upon administration by the chosen route to the chosen site, result in an effective concentration are referred to as effective amounts of the SMR in question. How an effective amount of an SMR that results in an effective concentration can be determined is well within the skills of an artisan.

In the afore-described specific example of how the novel immunization method may be practiced, a heat- and SMR-controlled RCCHV of the present disclosure and an appropriate SMR were co-administered in a single composition. RCCHV and SMR can also be administered in separate compositions. Topical co-administration of immunizing virus and SMR appears advantageous for several reasons, including minimization of potential secondary effects of the SMR, further reduction of the already remote possibility that virus may replicate systemically during the immunization period, and minimization of the environmental impact of elimination of SMR. Notwithstanding these advantages, the SMR may be given by a systemic route, e.g., orally, which may be preferred if a formulation of the drug substance of choice is already available that has been tested for a particular route of administration. The relative timing of inoculation with RCCHV, administration of an appropriate heat dose and administration of an effective amount of SMR is derivative of the operational requirements of dual-responsive gene switch control. Typically, inoculation with immunizing virus will precede heat treatment. This is because heat activation of HSF1 is transient, and activated factor returns to an inactive state within at most a few hours after activation. The dual-responsive transactivator gene present in the viral genome must be available for HSF1-mediated transcription during the latter short interval of factor activity. For the latter gene(s) to become available for transcription, the immunizing virus will have had to adsorb to a host cell, enter the cell and unravel to present its genome to the cellular transcription machinery. Although not preferred, it is possible to heat-expose the inoculation site region immediately after (or even shortly before) administration of the immunizing virus. Typically, the inoculation site region is heat-exposed at a time between about 30 min to about 10 h after virus administration, although heat treatment may be administered even later. Regarding administration of the SMR, there typically will be more flexibility because it will be possible to maintain an effective concentration systemically or specifically in the inoculation site region for one to several days. Consequently, SMR can be administered prior to, at the time of or subsequent to virus administration, the only requirement being that the regulator be present in an effective concentration in the inoculation site region for the time needed for the target transactivator to fulfill its role in enabling viral replication. Typically, this time will correspond to that required for the completion of a round of induced virus replication. Typically, a round of virus replication will be completed within about one day.

As has been alluded to before, in the novel immunization method an RCCHV may be induced to replicate once or several times. Replication may be re-induced one to several days after the previous round of replication. Such repeated replication will serve to increase viral load in the subject. For any round of replication to occur, the target cells that are infected with RCCHV need to receive an activating heat dose and the tissue of which the latter cells are part (the inoculation site region) must contain an effective concentration of small-molecule regulator.

Inoculation can be by any suitable route. The body region (inoculation site region) to which an RCCHV is administered may typically be a cutaneous or subcutaneous region located anywhere on the trunk or the extremities of a subject. Preferably, administration of a composition of the invention comprising an RCCHV may be to a cutaneous or subcutaneous region located on an upper extremity of the subject. Administration may also be to the lungs or airways, a mucous membrane in an orifice of a subject or any other tissue region in which the virus is capable of replicating.

The heat- and SMR-controlled RCCHVs exemplified herein are controlled by a heat- and antiprogestin-coactivated gene switch. They express mifepristone- or ulipristal-activated chimeric transactivator GLP65 (or glp65). This transactivator comprises a DNA-binding domain from yeast transcription factor GAL4, a truncated ligand-binding domain from a human progesterone receptor and a transactivation domain from the human RelA protein (p65). Burcin et al. (1999); Ye et al. (2002). Other exemplary SMR-activated transactivators than can be incorporated in an RCCHV include tetracycline/doxycycline-regulated tet-on repressors (Gossen & Bujard (1992) Proc Natl Acad Sci USA 89: 5547-51; Gossen et al. (1996) Science 268: 1766-69), and transactivators containing a ligand-binding domain of an insect ecdysone receptor (No et al. (1996) Proc Natl Acad Sci USA 93: 3346-51). A stringently ligand-dependent transactivator of this type is the RheoSwitch transactivator developed by Palli and colleagues (Palli et al. (2003) Eur J Biochem 270: 1308-15; Kumar et al. (2004) J Biol Chem 279: 27211-18). The RheoSwitch transactivator can be activated by ecdysteroids such as ponasterone A or muristerone A, or by synthetic diacylhydrazines such as RSL-1 (also known as RH-5849). Dhadialla et al. (1998) Annu Rev Entomol 43: 545-69. Other SMR-activated transactivators may be used, provided that they can be employed to control the activity of a target gene without also causing widespread deregulation of genes in cells of the intended hosts (subjects) and provided further that the associated SMRs have acceptably low toxicity in the hosts at their effective concentrations.

A concern has been whether pre-existing immunity to a virus will preclude its use as a vaccine or oncolytic vector. This issue not only relates to viruses such as adenoviruses and herpesviruses that are endemic but also to viruses that not normally infect humans but are used repeatedly as vectors. There may have been more serious concerns regarding the effects of pre-existing immunity to adenovirus (type 5) than to any other vector. Draper & Heeney (2010) Nat Rev Microbiol 8: 62-73. Steffensen et al. (2012) (PLoS ONE (2012) 7: e34884) demonstrated that pre-existing immunity does not interfere with the generation of memory CD8 T cells upon vaccination with a heterologous antigen-expressing modified Ad5 vector, providing a basis for an efficient recall response and protection against subsequent challenge. Furthermore, the transgene product-specific response could be boosted by re-vaccination. The issue of pre-existing immunity to herpesviruses has also been examined in multiple studies. Brockman & Knipe (2002) J Virol 76: 3678-87; Chahlavi et al. (1999) Gene Ther 6: 1751-58; Delman et al. (2000) Hum Gene Ther 11: 2465-72; Hocknell et al. (2002) J Virol 76: 5565-80; Lambright et al. (2000) Mol Ther 2: 387-93; Herrlinger et al. (1998) Gene Ther 5: 809-19; Lauterbach et al. (2005 J Gen Virol 86: 2401-10; Watanabe et al. (2007) Virology 357: 186-98. A majority of these studies reported little effect or only relatively minor effects on immune responses to herpesvirus-delivered heterologous antigens or on anti-tumor efficacy of oncolytic herpesviruses. Brockman & Knipe (2002); Chahlavi et al. (1999); Delman et al. (2000); Hocknell et al. (2002); Lambright et al. (2000); Watanabe, D (2007). Two studies reported substantial reductions of immune responses. Herrlinger (1998); Lauterbach et al. (2005). However, it appears that the results of these studies may not be generalized because compromised models were employed. One of the studies employed a tumor model that was only barely infectable with the mutant HSV strain used. Herrlinger (1998). The other study employed a chimeric mouse immune model in combination with a severely crippled HSV strain (ICP4−, ICP22−, ICP27−, vhs−) as the test vaccine. Lauterbach et al. (2005). All studies agreed that vaccine uses of herpesviruses are possible even in the presence of pre-existing immunity. It may be added that pre-existing immunity, e.g., to herpesviruses, may not be of general concern for childhood preventative or therapeutic interventions.

Herpesviruses have evolved a multitude of mechanisms for evading immune detection and avoiding destruction. Tortorella et al. (2000) Annu Rev Immunol 18: 861-926. Elimination or weakening of some of these mechanisms could further enhance the potency of an RCCHV. For example, HSV-1 and HSV-2 express protein ICP47. This protein binds to the cytoplasmic surfaces of both TAP1 and TAP2, the components of the transporter associated with antigen processing TAP. Advani & Roizman (2005) In: Modulation of Host Gene Expression and Innate Immunity by Viruses (ed. P. Palese), pp. 141-61, Springer Verlag. ICP47 specifically interferes with MHC class I loading by binding to the antigen-binding site of TAP, competitively inhibiting antigenic peptide binding. Virus-infected human cells are expected to be impaired in the presentation of antigenic peptides in the MHC class I context and, consequently, to be resistant to killing by CD8+ CTL. Deletion or disablement of the gene that encodes ICP47 ought to significantly increase the potency of an RCCHV (both as an oncolytic agent and as a vaccine).

The potency of an RCCHV may also be enhanced by including in the viral genome an expressible gene for a cytokine or other component of the immune system. A vaccination study in mice in which replication-defective herpesvirus recombinants expressing various cytokines were compared demonstrated that virus-expressed IL-4 and IL-2 had adjuvant effects. Osiorio & Ghiasi (2003) J Virol 77: 5774-83. Further afield, modulation of dendritic cell function by GM-CSF was shown to enhance protective immunity induced by BCG and to overcome non-responsiveness to a hepatitis B vaccine. Nambiar et al. (2009) Eur J Immunol 40: 153-61; Chou et al. (2010) J Immunol 185: 5468-75.

Expanding upon the basic definition given on p. 8 as it relates to vaccine uses, an effective amount of an RCCHV of the present disclosure is an amount that upon administration to a subject and induced replication therein results in a detectably enhanced functional immunity of the subject (that is typically superior to the immunity induced by a replication-defective comparison virus or the unactivated RCCHV). This enhanced functional immunity may manifest itself as enhanced resistance to infection or re-infection with a circulating (wild type) virus or may relate to enhanced suppression/elimination of a current infection. Hence, it may manifest itself by a reduced disease severity, disease duration or mortality subsequent to infection with said wild type virus. Alternatively, or in addition, in the case of an immunizing RCCHV expressing a foreign (heterologous) antigen, immunity can relate to preventive or therapeutic immunity against pathogens expressing and/or displaying the latter foreign antigen. It is noted that a number of factors will influence what constitutes an effective amount of an RCCHV, including to some extent the site and route of administration of the virus to a subject as well as the precise activation regimen utilized. Effective amounts of an RCCHV will be determined in dose-finding experiments. Generally, for vaccine uses, an effective amount of an RCCHV of the present disclosure will be from about 102 to about 109 plaque-forming units (pfu) of virus. More preferably, an effective amount will be from about 103 to about 108 pfu of virus, and even more preferably from about 103 to about 107 pfu of virus. Larger amounts may be indicated, in particular for oncolytic therapies.

A composition of the invention will comprise an effective amount of an RCCHV and, if an SMR is also administered as part of the composition, an effective amount of the SMR. It further comprises, typically, a pharmaceutically acceptable carrier or excipient. Although it may be administered in the form of a fine powder, e.g., a lyophilizate, under certain circumstances (see, e.g., U.S. Pat. Appl. Publ. No 20080035143; Chen et al. (2017) J Control Release 255: 36-44), a composition of the invention typically is an aqueous composition comprising an RCCHV and, as the case may be, an SMR. It may be administered parenterally to a subject as an aqueous solution or, in the case of administration to a mucosal membrane (e.g., airways), possibly as an aerosol thereof. See, e.g., U.S. Pat. No. 5,952, 220. The term parenteral as used herein includes subcutaneous, intracutaneous (epidermis and/or dermis), intravenous, intramuscular, intraarticular, intraarterial, intrasynovial, intrasternal, intrathecal, intralesional and intracranial injection or infusion techniques.

The compositions of the present invention will typically include a buffer component. The compositions will have a pH that is compatible with the intended use and is typically between about 6 and about 8. A variety of conventional buffers may be employed such as phosphate, citrate, histidine, Tris, Bis-Tris, bicarbonate and the like and mixtures thereof. The concentration of the buffer generally ranges from about 0.01 to about 0.25% w/v (weight/volume).

The compositions of the invention comprising am RCCHV can further include, for example, preservatives, virus stabilizers, tonicity agents and/or viscosity-increasing substances. As mentioned before, they may also include an appropriate SMR, or a formulation comprising such SMR.

Preservatives used in parenteral products include phenol, benzyl alcohol, methyl paraben/propylparaben and phenoxyethanol. Phenoxyethanol appears to be the most widely used preservative found in vaccines. Preservatives are generally used in concentrations ranging from about 0.002 to about 1% w/v. Meyer (2007) J Pharm Sci 96: 3155-67. Preservatives may be present in compositions comprising an RCCHV at concentrations at which they do not or only minimally interfere with the replication efficiency of the virus.

Osmolarity can be adjusted with tonicity agents to a value that is compatible with the intended use of the compositions. For example, the osmolarity may be adjusted to approximately the osmotic pressure of normal physiological fluids, which is approximately equivalent to about 0.9% w/v of sodium chloride in water. Examples of suitable tonicity-adjusting agents include, without limitation, chloride salts of sodium, potassium, calcium and magnesium, dextrose, glycerol, propylene glycol, mannitol, sorbitol and the like, and mixtures thereof. Preferably, the tonicity agent(s) will be employed in an amount to provide a final osmotic value of 150 to 450 mOsm/kg, more preferably between about 220 to about 350 mOsm/kg and most preferably between about 270 to about 310 mOsm/kg.

If indicated, the compositions of the present disclosure can further include one or more viscosity-modifying agents such as cellulose polymers, including hydroxypropylmethyl cellulose, hydroxyethyl cellulose, ethylhydroxyethyl cellulose, hydroxypropyl cellulose, methyl cellulose, carboxymethyl cellulose, glycerol, carbomers, polyvinyl alcohol, polyvinyl pyrrolidone, alginates, carrageenans, guar, karaya, agarose, locust bean, tragacanth and xanthan gums. Such viscosity modifying components are typically employed in an amount effective to provide the desired degree of thickening. Viscosity-modifying agents may be present in compositions comprising an RCCHV at concentrations at which they do not or only minimally interfere with the replication efficiency of the virus.

If the composition also contains an SMR, an effective amount of such SMR can be included in the composition in the form of a powder, solution, emulsion or particle. As also provided before, an effective amount of an SMR to be co-delivered with an effective amount of an RCCHV will be an amount that yields an effective concentration of the SMR in the inoculation site region, which effective concentration enables at least one round of replication of the RCCHV in infected cells of that region. To maintain an SMR at an effective concentration for a more extended period, it may be included in the form of a slow-release formulation (see also below).

Methods for amplifying herpesviruses are well known in the laboratory art. Industrial scale-up has also been achieved. Hunter (1999) J Virol 73: 6319-26; Rampling et al. (2000) Gene Ther 7: 859-866; Mundle et al. (2013) PLoS ONE 8(2): e57224. Various methods for purifying viruses have been disclosed. See, e.g., Mundle et al. (2013) and references cited therein; Wolf and Reichl (2011) Expert Rev Vaccines 10: 1451-75.

While an SMR can be co-administered with an RCCHV in a single composition, a composition comprising an RCCHV and a composition comprising an SMR can also be administered separately. The latter composition will comprise an effective amount of an SMR formulated together with one or more pharmaceutically acceptable carriers or excipients.

A composition comprising an SMR may be administered orally, parenterally, by inhalation spray, topically, rectally, nasally, buccally, vaginally or via an implanted reservoir, preferably by oral administration, administration by injection or deposition at the site of virus inoculation. The compositions may contain any conventional non-toxic, pharmaceutically acceptable carrier, adjuvant or vehicle. In some cases, the pH of the formulation may be adjusted with pharmaceutically acceptable acids, bases or buffers to enhance the stability of the formulated SMR or its delivery form.

Liquid dosage forms of an SMR for oral administration include pharmaceutically acceptable emulsions, microemulsions, solutions, suspensions, syrups and elixirs. In addition, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include, e.g., wetting agents, emulsifying and suspending agents, sweetening, flavoring, and perfuming agents.

Injectable preparations, for example sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic, parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

In order to prolong the effect of an SMR, it may be desirable to slow the absorption of the compound from, e.g., subcutaneous, intracutaneous or intramuscular injection. This may be accomplished by the use of a liquid suspension of crystalline or amorphous material with poor water solubility. The rate of absorption of the SMR then depends upon its rate of dissolution, which, in turn, may depend upon crystal size and crystalline form. Alternatively, delayed absorption of a parenterally administered SMR is accomplished by dissolving or suspending the compound in an oil vehicle. Injectable depot forms are made by forming microcapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration can be suppositories which can be prepared by mixing the SMR with suitable non-irritating excipients or carriers such as cocoa butter, polyethylene glycol or a suppository wax which are solid at ambient temperature but liquid at body temperature and therefore melt in the rectum or vaginal cavity and release the SMR.

Solid dosage forms for oral administration include capsules, tablets, pills, powders, and granules. In such solid dosage forms, the SMR is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution-retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the SMR only, or preferentially, in a certain part of the intestinal tract, optionally, in a delayed manner. Examples of embedding compositions that can be used include polymeric substances and waxes.

Dosage forms for topical, intradermal or transdermal administration of an SMR include ointments, pastes, creams, lotions, gels, powders, solutions, sprays, inhalants or patches. The SMR is admixed under sterile conditions with a pharmaceutically acceptable carrier and any preservatives or buffers as may be required.

The ointments, pastes, creams and gels may contain, in addition to an SMR, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the SMR, excipients such as lactose, talc, silicic acid, aluminum hydroxide, calcium silicates and polyamide powder, or mixtures of these substances. Sprays can additionally contain customary propellants.

Transdermal patches have the added advantage of providing controlled delivery of a compound. Such dosage forms can be made by dissolving or dispensing the compound in the proper medium. Absorption enhancers can also be used to increase the flux of the compound into or across the skin.

For pulmonary delivery, a composition comprising an effective amount of an SMR is formulated and administered to the subject in solid or liquid particulate form by direct administration e.g., inhalation into the respiratory system. Solid or liquid particulate forms of the SMR prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. Nos. 5,767,068 and 5,508,269, and WO 98/43650). A discussion of pulmonary delivery of antibiotics is also found in U.S. Pat. No. 6,014, 969.

What an effective amount of an SMR is will depend on the activity of the particular SMR employed, the route of administration, time of administration, the stability and rate of excretion of the particular SMR as well as the nature of the specific composition administered. It may also depend on the age, body weight, general health, sex and diet of the subject, other drugs used in combination or contemporaneously with the particular SMR employed and like factors well known in the medical arts.

Ultimately, what is an effective amount of an SMR can be determined in dose-finding experiments, in which replication of a heat- and SMR-controlled RCCHV is assessed experimentally in the inoculation site region. Once an effective amount has been determined in animal experiments, it may be possible to estimate a human effective amount. "Guidance for Industry. Estimating the maximum safe starting dose for initial clinical trials for therapeutics in adult healthy volunteers", U.S. FDA, Center for Drug Evaluation and Research, July 2005, Pharmacology and Toxicology. For example, as estimated from rat data, an effective human amount of orally administered mifepristone (for enabling at least one cycle of virus replication) will be between about 1 and about 100 μg/kg body weight.

Recitation of ranges of values herein are merely intended to serve as a shorthand method of referring individually to each separate value falling within the range, unless otherwise indicated herein, and each separate value is incorporated into the specification as if it were individually recited herein. The singular encompasses the plural, unless otherwise stated or clearly contradicted by context.

The description herein of any aspect or embodiment of the invention using terms such as reference to an element or elements is intended to provide support for a similar aspect or embodiment of the invention that "consists of"," "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The present invention, thus generally described, will be understood more readily by reference to the following examples, which are provided by way of illustration and are not intended to be limiting of the present invention.

EXAMPLES

Example 1: Isolation and Characterization of Mouse KRT1 and KRT77 Promoters

KRT1 and KRT77 promoter and RNA leader sequences were PCR-amplified from mouse genomic DNA using a standard protocol. Promoter sequences lie upstream from the start of transcription site (−), and RNA leader sequences begin at the start of transcription site (+). PCR amplification employed either primers mKRT1F1 (5"-CTGACTGGCTT- TAGCCCCTT-3') (SEQ ID NO: 1) and mKRT1R1 (5'-GCCTTAGAGAGAGGTGAGAGC-3') (SEQ ID NO: 2), or primers mKRT1F2 (5'-GCCACAAAACACTTTCAGGTACATA-3') (SEQ ID NO: 3) and mKRT1R2 (5"-TGATGCCT-TAGAGAGAGGTGA-3') (SEQ ID NO: 4). For KRT77, the primers were mKRT77F1 (5"-AAGATTTATT-AGTGCGTTTTGGTGC-3') (SEQ ID NO: 5) and mKRT77R1 (5"-CAGAAGCACTGGTAGCAAGGA-3') (SEQ ID NO: 6). The latter primer sequences were designed based on published mKRT1 and mKRT77 sequences (FIGS. 1 and 2) (SEQ ID NOS: 7 and 8). The amplified KRT1 and KRT77 segments were then subcloned into vector pGL4.16 (Promega Corp., Madison, WI) that contains a promoter-less luciferase reporter gene luc2CP from Photinus pyralis. To achieve this, the amplified KRT1 and KRT77 DNAs were further amplified with forward and reverse primers that also contained a KpnI or a BamHI recognition sequence, respectively. The re-amplified DNAs were digested with KpnI and BamHI, and the fragments were gel-purified and then ligated into KpnI/BgII-double-digested pGL4.16. Following transformation, colonies were picked and expanded, and inserts were subjected to nucleotide sequence analysis. Clone KRT1 1.2 contains mKRT1 sequences from position −993 to position +56, clone KRT1 2.3 mKRT1 sequences from position −1026 to position +60 and clone KRT77 3.2 mKRT77 sequences from position −986 to position +72.

The ability of the KRT promoters to drive transcription from the functionally linked luciferase reporter gene was assessed in several cell types. Since expression was to be compared between different cell types which may differ in transfectability and general transcriptional activity, the different KRT constructs were co-transfected with a construct that contained a β-galactosidase reporter gene controlled by the ubiquitously active ROSA promoter (pDRIVE-mROSA; InvivoGen Corp.). Transfection of subconfluent cultures grown under standard conditions employed a standard lipofectamine procedure. The activities of the KRT promoters were expressed as ratios of relative luciferase (LUC) to β-galactosidase (B-GAL) activities. LUC activity was measured using the Dual Glo Luciferase Assay System (Promega) and BGAL activity using the Beta-Glo Assay System (Promega).

TABLE 2

Activity of KRT promoters in Neuro2a cells

| Construct | Rel. LUC activity | Rel. LUC activity-pGL4.16 vector background | Rel. B-GAL activity (− background) | LUC/(B-GAL × $10^{-4}$) |
| --- | --- | --- | --- | --- |
| KRT1 1.2 | 70.5 +/− 7.3 | 13.7 | 130073.7 +/− 6589 | 1.0 |
| KRT1 2.3 | 91.0 +/− 12.0 | 34.2 | 136262.3 +/− 3389 | 2.5 |
| KRT77 3.2 | 55.3 +/− 29.6 | 0 | 131378.7 +/− 6127 | 0 |
| pGL4.16 (promoter-less) | 56.8 +/− 36.8 |  | 112490.0 +/− 5862 |  |

TABLE 3

Activity of KRT promoters in HEK293T cells

| Construct | Rel. LUC activity | Rel. LUC activity-pGL4.16 vector background | Rel. B-GAL activity (− background) | LUC/(B-GAL × $10^{-4}$) |
| --- | --- | --- | --- | --- |
| KRT1 1.2 | 9500.9 +/− 1029 | 8400.8 | 36006.0 +/− 3995.9 | 2333.5 |
| KRT1 2.3 | 6051.6 +/− 1486 | 4951.5 | 41178.5 +/− 1267.1 | 1201.8 |
| KRT77 3.2 | 20990 +/− 2313 | 19889.9 | 42632.5 +/− 3459.5 | 4668.9 |
| pGL4.16 (promoter-less) | 1100.1 +/− 172 |  | 36409.2 +/− 8205.9 |  |

Results from two representative experiments are shown in Tables 2 and 3. The experiment in Table 2 was conducted employing mouse neural cell line Neuro2a, and the experiment in Table 3 with the human epithelial cell line HEK293T. The results demonstrate clearly that the KRT1 and KRT77 promoters are highly active in the epithelial cells but essentially inactive in the neural cells. Therefore, the isolated promoter segments contain all information required for their cell type-specific activity.

Example 2: Construction of Heat- and Antiprogestin-Controlled RCCHVs HSV-GS1 and HSV-GS3

The generation of the viral recombinants was performed by homologous recombination of engineered plasmids along with purified virion DNA into rabbit skin cells (RS) (or HEK293T cells in other Examples) by the calcium phosphate precipitation method as previously described. Bloom (1998) HSV (Methods Mol Med (1998) 10: 369-386). All plasmids used to engineer the insertions of heat shock promoters (HSP70B promoters in the example constructions described herein), transactivators or the GAL4-responsive promoters for recombination into the HSV-1 genome were cloned from HSV-1 strain 17syn+. Plasmid IN994 was created as follows: an HSV-1 upstream recombination arm was generated by amplification of HSV-1 DNA (from base pairs 95,441 to 96,090) with DB112 (5'GAG CTC ATC ACC GCA GGC GAG TCT CTT3') (SEQ ID NO: 9) and DB113 (5'GAG CTC GGT CTT CGG GAC TAA TGC CTT3') (SEQ ID NO: 10). The product was digested with SacI and inserted into the SacI restriction site of pBluescript to create pUP. An HSV-1 downstream recombination arm was generated using primers DB115-KpnI (5'GGG GTA CCG GTT TTG TTT TGT GTG AC3') (SEQ ID NO: 11) and DB120-KpnI (5'GGG GTA CCG GTG TGT GAT TTC GC3') (SEQ ID NO: 12) to amplify HSV-1 genomic DNA sequence between base pairs 96,092 and 96,538. The PCR product was digested with KpnI, and cloned into KpnI digested pUP to create pIN994, which recombines with HSV-1 at the intergenic UL43/44 region.

HSV-GS1

HSV-GS1 contains a transactivator (TA) gene cassette inserted into the intergenic region between UL43 and UL44. In addition, the ICP4 promoter has been replaced with a GAL4-responsive promoter (GAL4-binding site-containing minimal promoter) in both copies of the short repeats. A first recombination plasmid pIN:TA1 was constructed by inserting a DNA segment containing a GLP65 gene under the control of a promoter cassette that combined a human HSP70B (heat shock) promoter and a GAL4-responsive promoter (described in Vilaboa et al. (2005)) into the multiple cloning site of plasmid pIN994, between flanking sequences of the HSV-1 UL43 and UL44 genes. The TA cassette was isolated from plasmid Hsp70/GAL4-GLP65 (Vilaboa et al. (2005)) and was cloned by 3-piece ligation to minimize the region that was amplified by PCR. For the left insert, Hsp70/GAL4-GLP65 was digested with BamHI and BstX1 and the resulting 2875 bp band was gel-purified. This fragment contains the Hsp70/GAL4 promoter cassette as well as the GAL4 DNA-binding domain, the progesterone receptor ligand-binding domain and part of the p65 activation domain of transactivator GLP65. The right insert was generated by amplifying a portion of pHsp70/GAL4-GLP65 with the primers TA.2803-2823.fwd (5'TCG ACA ACT CCG AGT TTC AGC3') (SEQ ID NO: 13) and BGHpA.rev (5' CTC GCG GCC GCA TCG ATC CAT AGA GCC CAC CGC ATC C3') (SEQ ID NO: 14). The 763 bp PCR product was digested with BstX1 and NotI, and the resultant 676 bp band was gel-purified. This band contained the 3'end of the p65 activation domain and the BGHpA. For the vector, pIN994 was digested with BamHI and NotI, and the resulting 4099 bp fragment was gel-purified and shrimp alkaline phosphatase (SAP)-treated. The two inserts were then simultaneously ligated into the vector, creating an intact TA cassette. Subsequent to transformation, colony #14 was expanded, and the plasmid was verified by restriction enzyme analysis and then by sequence analysis.

One μg of pIN:TA1 was co-transfected with 2 μg of purified HSV-1 (17+) virion DNA into RS cells by calcium phosphate precipitation. The resulting pool of viruses was screened for recombinants by picking plaques, amplifying these plaques on 96 well plates of RS cells, and dot-blot hybridization with a $^{32}$P-labeled DNA probe prepared by labeling a TA fragment by random-hexamer priming. A positive well was re-plaqued and re-probed 5 times and verified to contain the TA by PCR and sequence analysis. This intermediate recombinant was designated HSV-17GS43.

A second recombination plasmid, pBS-KS:GAL4-ICP4, was constructed that contained a GAL4-responsive promoter inserted in place of the native ICP4 promoter by cloning it in between the HSV-1 ICP4 recombination arms in the plasmid pBS-KS:ICP4Δpromoter. This placed the ICP4 transcript under the control of the heterologous GAL4 promoter. This particular promoter includes six copies of the yeast GAL4 UAS (upstream activating sequence), the adenovirus E1b TATA sequence and the synthetic intron Ivs8. This promoter was excised from the plasmid pGene/v5-HisA (Invitrogen Corp.) with AatII and HindIII, and the resulting 473 bp fragment was gel-purified. For the vector, pBS-KS:ICP4Δ promoter was digested with AatII and HindIII and the resulting 3962 bp fragment gel-purified and SAP-treated. Ligation of these two fragments placed the GAL4 promoter in front of the ICP4 transcriptional start-site. Subsequent to transformation, colony #5 was expanded, test-digested and verified by sequencing.

One μg of pBS-KS:GAL4-ICP4 was co-transfected with 4 μg of purified HSV-17GS43 virion DNA into cells of the ICP4-complementing cell line E5 (DeLuca and Schaffer (1987) Nucleic Acids Res 15: 4491-4511) by calcium phosphate precipitation. The resulting pool of viruses was screened for recombinants by picking plaques, amplifying these plaques on 96 well plates of E5 cells, and dot-blot hybridization with a $^{32}$P-labeled DNA probe prepared by labeling the GAL4-responsive promoter fragment by random-hexamer priming. A positive well was re-plaqued and re-probed 7 times and verified to contain the GAL4-responsive promoter in both copies of the short repeat sequences by PCR and sequence analysis. This recombinant was designated HSV-GS1.

To obtain pBS-KS:ΔSacI, the SacI site was deleted from the polylinker of plasmid vector pBluescript-KS+, by digesting the plasmid with SacI. The resulting 2954 bp fragment was gel-purified, treated with T4 DNA polymerase to produce blunt ends, re-circularized and self-ligated. Recombination plasmid BS-KS:ICP4Δ promoter was constructed as follows: to generate a first insert, cosmid COS48 (a gift of L. Feldman) was subjected to PCR with the primers HSV1.131428-131404 (5' CTC AAG CTT CTC GAG CAC ACG GAG CGC GGC TGC CGA CAC G3') (SEQ ID NO: 15) and HSV1.130859-130880 (5' CTC GGT ACC CCA TGG AGG CCA GCA GAG CCA GC3') (SEQ ID NO: 16). The primers placed HindIII and XhoI sites on the 5' end of the region and NcoI and KpnI sites on the 3' end, respectively. The 600 bp primary PCR product was digested with HindIII and KpnI, and the resulting 587 bp fragment was gel-purified. Vector pBS-KS:ΔSacI was digested with HindIII and KpnI, and the resulting 2914 bp fragment was gel-purified and SAP-treated. Ligation placed the first insert into the vector's polylinker, creating pBS-KS:ICP4-3'end. To generate a second insert, cosmid COS48 was subjected to PCR with the primers HSV1.132271-132250 (5' CTC GCG GCC GCA CTA GTT CCG CGT GTC CCT TTC CGA TGC3') (SEQ ID NO: 17) and HSV1.131779-131800 (5' CTC GAG AAG CTT ATG CAT GAG CTC GAC GTC TCG GCG GTA ATG AGA TAC GAG C3') (SEQ ID NO: 18). These primers placed NotI and SpeI sites on the 5' end of the region and AatII, SacI, NsiI, HindIII and XhoI sites on the 3' end, respectively. The 549 bp primary PCR product was digested with NotI and XhoI, and the resulting 530 bp band was gel-purified. This fragment also contained the 45 bp OriS hairpin. Plasmid BS-KS:ICP4-3' end was digested with NotI and XhoI and the resulting 3446 bp band was gel-purified and SAP-treated. Ligation generated pBS-KS:ICP4Δ promoter. The inserts in pBS-KS:ICP4Δ promoter were verified by sequence analysis.

HSV-GS3 contains a transactivator (TA) gene cassette inserted into the intergenic region between UL43 and UL44. In addition, the ICP4 promoter has been replaced with a GAL4-responsive promoter (GAL4-binding site-containing minimal promoter) in both copies of the short repeats. Furthermore, the ICP8 promoter was replaced with a GAL4-responsive promoter. The construction of this recombinant virus involved placing a second HSV-1 replication-essential gene (ICP8) under control of a GAL4-responsive promoter. HSV-GS1 was used as the "backbone" for the construction of this recombinant. ICP8 recombination plasmid pBS-KS:GAL4-ICP8 was constructed. This plasmid contained a GAL4-responsive promoter inserted in place of the native ICP8 promoter by cloning it in between the HSV-1 ICP8 recombination arms in the plasmid pBS-KS:ICP8Δpromoter. This placed the ICP8 transcript under the control of the heterologous GAL4-responsive promoter. This GAL4-responsive promoter was excised from the plasmid pGene/v5-HisA (Invitrogen Corp.) with AatII and HindIII, and the resulting 473 bp fragment was gel-purified. For the vector, pBS-KS:ICP8Δpromoter was digested with AatII and HindIII, and the resulting 4588 bp fragment gel-purified and SAP-treated. Ligation of the latter two DNA fragments placed the GAL4-responsive promoter cassette in front of the ICP8 transcriptional start-site. Subsequent to transformation, colony #10 was expanded, test-digested and verified by sequencing.

One μg of pBS-KS:GAL4-ICP8 was co-transfected with 10 μg of purified HSV-GS1 virion DNA into E5 cells by calcium phosphate precipitation. Subsequent to the addition of mifepristone to the medium, the transfected cells were exposed to 43.5° C. for 30 minutes and then incubated at 37° C. Subsequently, on days 2 and 3, the cells were again incubated at 43.5° C. for 30 minutes and then returned to 37° C. Plaques were picked and amplified on 96 well plates of E5 cells in media supplemented with mifepristone. The plates were incubated at 43.5° C. for 30 minutes 1 hour after infection and then incubated at 37° C. Subsequently, on days 2 and 3, the plates were also shifted to 43.5° C. for 30 minutes and then returned to 37° C. After the wells showed 90-100% CPE, the plates were dot-blotted and the dot-blot membrane hybridized with a $^{32}$P-labeled DNA probe prepared by labeling the HSV-1 ICP8 promoter fragment that was deleted. A faintly positive well was re-plaqued and re-probed 8 times and verified to have lost the ICP8 promoter and to contain the GAL4-responsive promoter in its place by PCR and sequence analysis. This recombinant was designated HSV-G53.

Recombination plasmid pBS-KS:ICP8Δpromoter was constructed using essentially the same strategy as that described above for the creation of pBS-KS:ICP4Δ promoter: a first insert was PCR-amplified from HSV-1 17syn+ virion DNA using the primers HSV1.61841-61865 (5' CTC AGA ACC CAG GAC CAG GGC CAC GTT GG3') (SEQ ID NO: 19) and HSV1.62053-62027 (5' CTC ATG GAG ACA AAG CCC AAG ACG GCA ACC3') (SEQ ID NO: 20) and subcloned to yield intermediate vector pBS-KS:ICP8-3' end. A second insert was similarly obtained using primers HSV1.62173-62203 (5' CTC GGA GAC CGG GGT TGG GGA ATG AAT CCC TCC3') (SEQ ID NO: 21) and HSV1.62395-62366 (5' CTC GCG GGG CGT GGG AGG GGC TGG GGC GGA CC3') (SEQ ID NO: 22) and was subcloned into pBS-KS:ICP8-3' end to yield pBS-KS:ICP8Δpromoter.

Example 3: Construction of Heat-Controlled RCCHVs: HSV-GS51-52

HSV-GS51 and HSV-GS52 contain ICP4 genes that are controlled by a human HSP70B promoter. Furthermore, the promoter of the UL38/VP19c gene is replaced with the mouse KRT77 promoter in HSV-GS51 and the mouse KRT1 promoter in HSV-GS52, respectively.

HSV-GS51

HSV-1 wildtype strain syn+ is used as the "backbone" for the construction of this recombinant. ICP4 recombination plasmid pBS-KS:HSP70B-ICP4 is constructed that contains a human HSP70B promoter inserted in place of the native ICP4 promoter by cloning it in between the HSV-1 ICP4 recombination arms in the plasmid pBS-KS:ICP4Δ promoter. To isolate a human HSP70B promoter fragment, construct p17 is digested with BamHI, ends are filled in by Klenow DNA polymerase, and the DNA is further digested with HindIII. A 0.45 kbp (kbp=1,000 bp) promoter fragment is gel-purified (Voellmy et al. (1985) Proc. Natl. Acad. Sci. USA 82: 4949-53). For the vector, pBS-KS:ICP4Δ promoter is digested with ZraI and HindIII. The resulting 3.96 kbp fragment is gel-purified. Ligation of the latter two DNA fragments places the HSP70B promoter in front of the ICP4 transcriptional start-site. Subsequent to transformation, several colonies are expanded, and plasmid DNAs subjected to restriction and then sequence analysis to identify pBS-KS:HSP70B-ICP4.

To obtain pBS-KS:ΔSacI, the SacI site was deleted from the polylinker of plasmid vector pBluescript-KS+, by digesting the plasmid with SacI. The resulting 2.95 kbp fragment was gel-purified, treated with T4 DNA polymerase to produce blunt ends, re-circularized and self-ligated. Recombination plasmid BS-KS:ICP4Δ promoter was constructed as follows: to generate a first insert, cosmid COS48 (a gift of L. Feldman) was subjected to PCR with the primers HSV1.131428-131404 (5' CTC AAG CTT CTC GAG CAC ACG GAG CGC GGC TGC CGA CAC G3') (SEQ ID NO: 15) and HSV1.130859-130880 (5' CTC GGT ACC CCA TGG AGG CCA GCA GAG CCA GC3') (SEQ ID NO: 16). The primers placed HindIII and XhoI sites on the 5' end of the region and NcoI and KpnI sites on the 3' end, respectively. The 0.60 kbp primary PCR product was digested with HindIII and KpnI, and the resulting 0.59 kbp fragment was gel-purified. Vector pBS-KS:ΔSacI was digested with HindIII and KpnI, and the resulting 2.91 kbp fragment was gel-purified and SAP-treated. Ligation placed the first insert into the vector's polylinker, creating pBS-KS:ICP4-3'end. To generate a second insert, cosmid COS48 was subjected to PCR with the primers HSV1.132271-132250 (5' CTC GCG GCC GCA CTA GTT CCG CGT GTC CCT TTC CGA TGC3') (SEQ ID NO: 17) and HSV1.131779-131800 (5' CTC GAG AAG CTT ATG CAT GAG CTC GAC GTC TCG GCG GTA ATG AGA TAC GAG C3') (SEQ ID NO: 18). These primers placed NotI and SpeI sites on the 5' end of the region and AatII, SacI, NsiI, HindIII and XhoI sites on the 3' end, respectively. The 0.55 kbp primary PCR product was digested with NotI and XhoI, and the resulting 0.53 kbp band was gel-purified. This fragment also contained the 45 bp OriS hairpin. Plasmid BS-KS:ICP4-3' end was digested with NotI and XhoI and the resulting 3.45 kbp band was gel-purified and SAP-treated. Ligation generated pBS-KS:ICP4Δ promoter. The inserts in pBS-KS:ICP4Δ promoter were verified by sequence analysis.

One μg of pBS-KS:HSP70B-ICP4 is co-transfected with 10 μg of purified HSV-1 syn+ virion DNA into cells of the ICP4-complementing cell line E5 (DeLuca, N. A. and Schaffer, P. A. (1987)) by calcium phosphate precipitation. The resulting pool of viruses is screened for recombinants by picking plaques, amplifying these plaques on 96 well plates of E5 cells, and dot-blot hybridization with a $^{32}$P-labeled DNA probe prepared by labeling the HSP70B promoter fragment by random-hexamer priming. A positive well is re-plaqued and re-probed several times and verified to contain the HSP70B promoter in both copies of the short repeat sequences by PCR and sequence analysis. This intermediary recombinant is designated HSV-17GS51.

To place the UL38/VP19c gene under regulation of a mouse KRT77 promoter, plasmid pBS-KS:KRT77-UL38 is constructed as follows. Plasmid KRT77 3.2 is subjected to PCR amplification using primers mKRT77AF1 (5"-GGACTGACGTCAAGATTTATTAGTGCGTTT TGGTGC-3') (SEQ ID NO: 23) and mKRT77AR1 (5"-CAACCCGGGCAGAAGCACTGGT AGCAAGGA-3') (SEQ ID NO: 24). The amplified fragment containing KRT77 sequences from position −986 to position +72 is digested with AatII and SmaI and is gel-purified. For the vector, plasmid pBS-KS:UL38Δpromoter containing HSV-1 UL38 recombination arms is digested with HindII, ends are filled in using Klenow DNA polymerase, and the DNA is further digested with AatII. The resulting 4.28-kbp fragment is gel-purified and SAP-treated. The latter two fragments are ligated. Following transformation, several colonies are amplified and tested for the presence of KRT77 sequences by dot blot using a $^{32}$P-labeled KRT77 probe. A clone containing the complete KRT77 promoter and RNA leader sequence of pKRT77 3.2 as assessed by nucleotide sequence analysis is designated pBS-KS:KRT77-UL38. Plasmid pBS-KS:UL38Δpromoter was constructed by deletion of the region from −1 to −47 of the UL38 promoter, i.e., by synthesizing two PCR fragments (one 0.44 kbp and the other 0.55 kbp long) on either side of the deletion and cloning these into pBS II KS+.

To produce recombinant HSV-GS51, HEK293T cells are co-transfected with 1 μg of plasmid pBS-KS:KRT77-UL38 and 10 μg of purified HSV-17GS51 virion DNA by calcium phosphate precipitation. The transfected cells are exposed to 43.5° C. for 30 min and then incubated at 37° C. Subsequently, on days 2 and 3, the cells are again incubated at 43.5° C. for 30 min and then returned to 37° C. Plaques are picked and amplified on 96-well plates of RS. One hour after infection, the plates are incubated at 43.5° C. for 30 min and then further incubated at 37° C. Subsequently, on days 2 and 3, the plates are also shifted to 43.5° C. for 30 min and then returned to 37° C. After the wells show 90 to 100% cytopathic effect, the plates are dot blotted, and the dot blot membrane is hybridized with a $^{32}$P-labeled DNA probe prepared by labeling the mouse KRT77 promoter segment. A positive well is re-plaqued and re-probed several times, and is verified to have lost the UL38 promoter and to contain the KRT77 promoter in its place by PCR and sequence analysis. This recombinant is designated HSV-GS51. It is noted that for recombination and isolation of HSV-GS51 E5 cells previously transfected with a VP19c-expression plasmid such as pUL38FBpCl (Adamson et al. (2006) J Virol 80: 1537-1548) may be employed instead of HEK293T cells, circumventing the need for repeated heat treatments for virus amplification.

HSV-GS52

To place the UL38/VP19c gene under regulation of a mouse KRT1 promoter, plasmid pBS-KS:KRT1-UL38 is constructed as follows. Plasmid KRT1 1.2 is subjected to PCR amplification using primers mKRT1AF1 (5"-GGACTGACGTCTGACTGGCTTTAGCCCCTT-3") (SEQ ID NO: 25) and mKRT1AR1 (5"-CAACCCGG GCCT-TAGAGAGAGGTGAGAGC-3") (SEQ ID NO: 26). The amplified fragment containing KRT1 sequences from position −993 to position +56 is digested with AatII and SmaI and is gel-purified. For the vector, plasmid pBS-KS: UL38Δpromoter is digested with HindII, ends are filled in using Klenow DNA polymerase, and the DNA is further digested with AatII. The resulting 4.28-kbp fragment is gel-purified and SAP-treated. The latter two fragments are ligated. Following transformation, several colonies are amplified and tested for the presence of KRT1 sequences by dot blot using a $^{32}$P-labeled KRT1 probe. A clone containing the complete KRT1 promoter and leader sequence of pKRT1 1.2 as assessed by nucleotide sequence analysis is designated pBS-KS:KRT1-UL38.

HEK293T cells are co-transfected with 1 μg of plasmid pBS-KS:KRT1-UL38 and 10 μg of purified HSV-17GS51 virion DNA by calcium phosphate precipitation. The transfected cells are incubated and heat-treated, and plaques are picked and amplified as described for the construction of HSV-GS51. Dot blots are hybridized with a $^{32}$P-labeled KRT1 promoter DNA probe. A positive well is re-plaqued and re-probed several times, and is verified to have lost the UL38 promoter and to contain the KRT1 promoter in its place by PCR and sequence analysis. This recombinant is designated HSV-GS52.

Example 4: Construction of Heat-Controlled RCCHVs Expressing a Transactivator: HSV-GS53-54

HSV-GS53 contains ICP4 and ICP8 genes that are controlled by a GAL4-hHSF1 transactivator driven by a human HSP70B promoter. In HSV-GS54 the expression of the same viral genes is controlled by a GAL4-hHSF1 transactivator that is driven by a human HSP70B/GAL4 promoter cassette (i.e., a sequence acting as both a heat shock promoter and a transactivator-responsive promoter). Furthermore, the promoter of the UL38/VP19c gene is replaced with the mouse KRT1 promoter in both recombinants.

HSV-GS53

Plasmid CMV-hHSF1 contains in between the HindIII and EcoR1 sites of vector pcDNA3.1 a human HSF1 cDNA fragment that includes the entire 529 residues-long HSF1-coding sequence as well as upstream and downstream untranslated sequences (FIG. 3) (SEQ ID NO: 27). Baler et al. (1993) Mol Cell Biol 13: 2486-2496; Xia et al. (1999) Cell Stress Chaperon 4: 8-18. The single NotI site in pCMV-hHSF1 is destroyed by NotI digestion, filling-in using the Klenow fragment of DNA polymerase I, self-religation, transformation and isolation of a colony that lacks the NotI site. This plasmid is designated CMV-hHSF1-delNotI. A segment containing the sequence coding for hHSF1 residues 431-529 (encompassing the hHSF1 activation domain), 3'nontranslated sequences of hHSF1 and the BGHpA region (present in the cDNA3.1 vector) is PCR-amplified from pCMV-hHSF1-delNotI using primers HSF1F (5' GACGGTACCCCGACCTTGA CAGCAGCCTG) (SEQ ID NO: 28) and BGHpA.rev (5' CTCCTCGCGGCCGCATCGAT CCATAGAGCCCACCG-CATCC) (SEQ ID NO: 14). The amplified fragment is digested with KpnI and NotI. Vector pSG424 containing an expressible gene for a GAL4 DNA-binding domain (residues 1-147) is digested with HindIII and KpnI to release the GAL4(1-147)-encoding fragment that is gel-purified. This fragment and the above KpnI/NotI-digested PCR fragment from pCMV-hHSF1-delNotI are co-ligated into HindIII/Not-double-digested and SAP-treated vector pBlueScript II SK. The resulting plasmid that contains the GAL4-HSF1 transactivator-coding sequence is designated pGAL4/HSF1TA. Plasmid GAL4/HSF1TA is digested with HindIII and NotI, and the released transactivator-encoding fragment (1.48 kbp in length) is gel-purified. Construct p17 is digested with BamHI and HindIII. A 045 kbp human HSP70B promoter fragment is gel-purified (Voellmy et al. (1985)). The latter two fragments are co-ligated with a pIN994 BamHI/NotI vector fragment. (pIN994 is digested with BamHI and NotI, and the resulting 4.10 kbp fragment is gel-purified and SAP-treated.) The resulting recombination plasmid is designated pIN: HSP-TA. Plasmid IN994 was created as described under Example 2.

One μg of pIN: HSP-TA is co-transfected with 10 μg of purified HSV-GS3 virion DNA into E5 cells by calcium phosphate precipitation. The transfected cells are exposed to 43.5° C. for 30 minutes and then incubated at 37° C. Subsequently, on days 2 and 3, the cells are again incubated at 43.5° C. for 30 minutes and then returned to 37° C. Plaques are picked and amplified on 96 well plates of E5 cells. The plates are incubated at 43.5° C. for 30 minutes 1 hour after infection and then incubated at 37° C. Subsequently, on days 2 and 3, the plates are also shifted to 43.5° C. for 30 minutes and then returned to 37° C. After the wells show 90-100% CPE, the plates are dot-blotted and the dot-blot membrane hybridized with a $^{32}$P-labeled DNA probe prepared by labeling a 0.71 kbp BalI/EcoRI fragment from pCMV-hHSF1 (containing sequences coding for HSF1 residues 437-529 and 3'untranslated sequences). A strongly positive well is re-plaqued and re-probed several times and verified to have lost the HSP70/GAL4-GLP65 transactivator cassette and to contain in its place the HSP70B promoter-GAL4-HSF1 transactivator cassette by PCR and sequence analysis. This recombinant is designated HSV-17GS53.

One µg of pBS-KS:KRT1-UL38 is co-transfected with 10 µg of purified HSV-17GS53 virion DNA into HEK293T cells by calcium phosphate precipitation. The transfected cells are incubated and heat treated, and plaques are picked and amplified as described for the construction of HSV-GS51. Dot blots are hybridized with a $^{32}$P-labeled KRT1 promoter DNA probe. A positive well is re-plaqued and re-probed several times, and is verified to have lost the UL38 promoter and to contain the KRT1 promoter in its place by PCR and sequence analysis. This recombinant is designated HSV-G553.

HSV-GS54

This recombinant is constructed by the procedure described for HSV-G553 with the sole exception that the 0.45 kbp BamHI/HindIII HSP70B promoter fragment is substituted by a 1.06-kbp BamHI/HindIII HSP70B/GAL4 promoter fragment isolated from pHsp70/GAL-fLuc (Vilaboa et al. (2005)).

Example 5: Construction of Heat- and Antiprogestin-Controlled RCCHVs HSV-GS1A and HSV-GS3A Recombinant HSV-GS1 contains, inserted in the intergenic region between UL43 and UL44, a GLP65 transactivator (TA) gene that is under the (dual) control of an HSP70 and a GAL4-responsive promoter. In addition, the ICP4 promoter is replaced with a GAL4-responsive promoter (GAL4-binding site-containing minimal promoter) in both copies of the short repeats. In HSV-GS3, derived from HSV-GS1, the ICP8 promoter is also replaced with a GAL4-responsive promoter. In HSV-GS1A and HSV-GS3A, derived from HSV-GS1 and HSV-GS3 respectively, the UL38/VP19c gene is controlled by a mouse KRT1 promoter.

To produce recombinants HSV-GS1A or HSV-GS3A, HEK293T cells are co-transfected by calcium phosphate precipitation with 1 µg of pBS-KS:KRT1-UL38 (described under Example 3) and 10 µg of purified HSV-GS1 virion DNA (for HSV-GS1A) or HSV-GS3 virion DNA (for HSV-GS3A). Subsequent to the addition of mifepristone (10 nM) to the medium, the transfected cells are exposed to 43.5° C. for 30 minutes and then incubated at 37° C. Subsequently, on days 2 and 3, the cells are again incubated at 43.5° C. for 30 minutes and then returned to 37° C. Plaques are picked and amplified on 96 well plates of HEK293T cells in media supplemented with mifepristone. The plates are incubated at 43.5° C. for 30 minutes 1 hour after infection and then incubated at 37° C. Subsequently, on days 2 and 3, the plates are also shifted to 43.5° C. for 30 minutes and then returned to 37° C. After the wells show 90-100% CPE, the plates are dot-blotted and the dot-blot membrane hybridized with a $^{32}$P-labeled KRT1 promoter DNA probe. A positive well is re-plaqued and re-probed several times and verified to have lost the UL38 promoter and to contain the KRT1 promoter in its place by PCR and sequence analysis. This recombinant is designated HSV-GS1A or 3A, respectively.

Example 6: Construction of Heat- and Antiprogestin-Controlled RCCHV HSV-GS3B Recombinant HSV-GS3B contains inserted in the intergenic region between UL43 and UL44, a GLP65 transactivator (TA) gene that is under the (dual) control of an HSP70 and a GAL4-responsive promoter. In addition, the ICP4 and ICP8 promoters are replaced with a GAL4-responsive promoter (GAL4-binding site-containing minimal promoter). The UL38/VP19c gene is controlled by a mouse KRT1 promoter. Furthermore, the US12 gene is mutated to render its protein product (ICP47) nonfunctional.

ICP47 amino acid residue K31 was changed to G31, and R32 to G32. Neumann et al. (1997) J. Mol. Biol. 272: 484-492; Galocha et al. (1997) J. Exp. Med. 185: 1565-1572. A 500-bp ICP47-coding sequence-containing fragment was PCR-amplified from virion DNA of strain 17syn+. The fragment was PCR-amplified as two pieces (a "left-hand" and a "right-hand" piece), using two primer pairs. The mutations were introduced through the 5' PCR primer for the right-hand fragment. The resulting amplified left-hand and mutated right-hand fragments were subcloned into vector pBS, and the sequence in subclones was confirmed by sequence analysis. A subclone containing the 500-bp fragment with the desired mutations in ICP47 codons 31 and 32 was termed pBS:mut-ICP47.

One µg of pBS:mut-ICP47 was co-transfected with 10 µg of purified HSV-GS3 virion DNA into E5 cells by calcium phosphate precipitation. Subsequent to the addition of mifepristone to the medium, the transfected cells were exposed to 43.5° C. for 30 minutes and then incubated at 37° C. Subsequently, on days 2 and 3, the cells were again incubated at 43.5° C. for 30 minutes and then returned to 37° C. Plaques were picked and amplified on 96 well plates of E5 cells in media supplemented with mifepristone. The plates were incubated at 43.5° C. for 30 minutes 1 hour after infection and then incubated at 37° C. Subsequently, on days 2 and 3, the plates were also shifted to 43.5° C. for 30 minutes and then returned to 37° C. After the wells showed 90-100% CPE, the plates were dot-blotted and the dot-blot membrane hybridized with a $^{32}$P-labeled oligonucleotide probe to the mutated ICP47 region. A positive well was re-plaqued and re-probed several times and verified by sequence analysis to contain the expected mutated ICP47 gene sequence. This recombinant was designated HSV-GS4.

To produce recombinant HSV-GS3B, HEK293T cells are co-transfected by calcium phosphate precipitation with 1 µg of pBS-KS:KRT1-UL38 (described under Example 3) and 10 µg of purified HSV-GS4 virion DNA. Subsequent to the addition of mifepristone (10 nM) to the medium, the transfected cells are exposed to 43.5° C. for 30 minutes and then incubated at 37° C. Subsequently, on days 2 and 3, the cells are again incubated at 43.5° C. for 30 minutes and then returned to 37° C. Plaques are picked and amplified on 96 well plates of HEK293T cells in media supplemented with mifepristone. The plates are incubated at 43.5° C. for 30 minutes 1 hour after infection and then incubated at 37° C. Subsequently, on days 2 and 3, the plates are also shifted to 43.5° C. for 30 minutes and then returned to 37° C. After the wells showed 90-100% CPE, the plates are dot-blotted and the dot-blot membrane hybridized with a $^{32}$P-labeled KRT1 promoter DNA probe. A positive well is re-plaqued and re-probed several times and verified to have lost the UL38 promoter and to contain the KRT1 promoter in its place by PCR and sequence analysis. This recombinant is designated HSV-GS3B.

Example 7: Construction of Heat- and Antiprogestin-Controlled RCCHV HSV-GS3C Recombinant HSV-GS3C contains inserted in the intergenic region between UL43 and UL44, a GLP65 transactivator (TA) gene that is under the control of an HSP70/GAL4 promoter cassette. In addition, the ICP4 and ICP8 promoters are replaced with GAL4-responsive promoters (GAL4-binding site-containing minimal promoters), and the UL38/VP19c gene is controlled by a mouse KRT77 promoter. Furthermore, the recombinant contains an insertion between the UL37 and UL38 genes of a gene cassette expressing the EIV Prague/56 hemagglutinin (HA) gene driven by the CMV IE promoter.

Recombinant HSV-GS11 was derived from the vector HSV-GS3 and contains an insertion between the UL37 and UL38 genes of a gene cassette expressing the A/Equine/Prague/1/56 (H7N7) hemagglutinin (HA) gene driven by the CMV IE promoter. The recombination plasmid was constructed by the following sequential steps. First, the 814 bp fragment containing the region spanning the HSV-1 UL37/UL38 intergenic region from nt 83,603-84,417 from the plasmid NK470 was subcloned into pBS SK+ that had had the MCS removed (digestion with KpnI/SacI) to yield pBS:UL37/38. A cassette containing a synthetic CMV IE promoter flanked by the pBS-SK+ MCS was ligated into pBS:UL37/38 that was digested with BspE1/AflII, which cuts between the UL37 and UL38 genes to yield the plasmid pIN:UL37/38. The EIV Prague/56 HA gene was PCR-cloned from cDNA prepared from EIV Prague/56. Briefly, RNA was prepared by Trizol extraction of a stock of EIV Prague/56 and reverse-transcribed using Omni-Script Reverse Transcriptase (Qiagen) according to the manufacturer's instructions. The cDNA was subcloned into pBS, and a clone containing the HA gene (pBS-EIVPrague56/HA) was confirmed by sequence analysis. The Prague/56 HA gene was excised from this plasmid and inserted behind the CMV promoter in the plasmid pIN:UL37/38 to yield plasmid pIN:37/38-Prague56/HA. To produce recombinant HSV-GS11, RS cells were co-transfected with plasmid pIN:37/38-Prague56/HA and purified HSV-GS3 virion DNA. Subsequent to the addition of mifepristone to the medium, the co-transfected cells were exposed to 43.5° C. for 30 min and then incubated at 37° C. Subsequently, on days 2 and 3, the cells were again incubated at 43.5° C. for 30 min and then returned to 37° C. Picking and amplification of plaques, screening and plaque purification was performed essentially as described for HSV-GS3. The resulting plaque-purified HSV-GS11 was verified by Southern blot as well as by PCR and DNA sequence analysis of the recombination junctions.

To produce recombinant HSV-GS3C, HEK293T cells are co-transfected by calcium phosphate precipitation with 1 μg of pBS-KS:KRT77-UL38 (described under Example 3) and 10 μg of purified HSV-GS11 virion DNA. Subsequent to the addition of mifepristone (10 nM) to the medium, the transfected cells are exposed to 43.5° C. for 30 minutes and then incubated at 37° C. Subsequently, on days 2 and 3, the cells are again incubated at 43.5° C. for 30 minutes and then returned to 37° C. Plaques are picked and amplified on 96 well plates of HEK293T cells in media supplemented with mifepristone. The plates are incubated at 43.5° C. for 30 minutes 1 hour after infection and then incubated at 37° C. Subsequently, on days 2 and 3, the plates are also shifted to 43.5° C. for 30 minutes and then returned to 37° C. After the wells show 90-100% CPE, the plates are dot-blotted and the dot-blot membrane hybridized with a $^{32}$P-labeled KRT77 promoter DNA probe. A positive well is re-plaqued and re-probed several times and verified to have lost the UL38 promoter and to contain the KRT77 promoter in its place by PCR and sequence analysis. This recombinant is designated HSV-GS3C.

Example 8: Analysis of Differential and Regulated Replication of RCCHVs in Epithelial and Neural Cells Stocks of RCCHVs HSV-GS51-54, HSV-GS1A, and HSV-GS3A-C can be propagated in HEK393T cells. Infected cultures are subjected to daily heat treatment at 43.5 (43-44) ° C. for 30 min for three successive days. For HSV-GS1A and HSV-GS3A-C, the medium is supplemented with 10 nM mifepristone.

Replication of an RCCHV and wildtype viral strain 17syn+ is compared in the epithelial cell line HEK293T and the neural cell line Neuro2a. HEK293T cells are grown in complete Dulbecco's modified Eagle's medium, supplemented with 10% fetal bovine serum and 2 mM I-glutamine and Neuro2a cells in in Eagle's Minimum Essential Medium plus 10% FBS. The ability of HSV-1 to infect and replicate in HEK293T and Neuro-2a cells has been documented previously. Zhao et al. (2016) Cell Host & Microbe 20: 770-784; Parker et al. (2000) Proc Natl Acad Sci USA 97: 2208-2213.

Confluent monolayers of target cells in multiple parallel plates are infected with virus (RCCHV or wildtype virus 17syn+) at a multiplicity of infection (MOI) of 3. Virus is allowed to adsorb for 1 h at 37° C., and then the inoculum is removed, and the cells are overlayed with medium. For cultures infected with an HSV-GS1A or HSV-GS3A-C recombinant, mifepristone treatment (10 nM) is initiated at the time of the initial infection or is omitted. Heat treatment is performed either immediately after infection or 4 h later by floating the sealed dishes in a 43.5° C. water bath for 30 min, or the heat treatment is omitted. The dishes are then incubated at 37° C. At 0, 4 or 8, 12 or 16, and 24 or 28 h postinfection, two dishes are removed, and the cells are scraped into medium for harvesting and subjected to two freeze-thaw cycles. Infectious virus is then determined by titrating the lysate of each dish in triplicate on 24-well plates of confluent E5 cells transfected 24 h prior to infection with expression plasmids pICP8 and pUL38FBpCl (Adamson et al. (2006)) using Lipofectamine 2000 (Life Technologies). Plaques are visualized after 2 days by staining with crystal violet. Alternatively, plaques are visualized 2 days after infection using an antibody plaque assay, essentially as previously described (Bewig and Schmidt (2000) Biotechniques 28: 870-873). Briefly, medium is removed, and the monolayers fixed with cold 100% methanol for 20 min at 20° C. The monolayers are then washed with phosphate-buffered saline (PBS) and, subsequent to addition of 100 μl of a 1/1000 dilution of a polyclonal anti-HSV antiserum (rabbit anti-HSV HRP conjugate, DAKO labs), are incubated for 1 h a room temperature. The antiserum is aspirated, the monolayers are rinsed twice with PBS, and the plaques are visualized by adding 200 μl of Immunopure DAB substrate (Pierce Chemicals), which is removed after approximately 10 min by rinsing with PBS.

To construct expression plasmid pICP8, a 3777 bp fragment containing the entire ICP8-coding sequence and the native promoter of the ICP8 gene was PCR-amplified from HSV-1 17syn+ virion DNA using primers HSV1.58409-58444 (CTCCTCTTTATTTTACACACATTCCCC GCCCCGCCCTAGGTT) (SEQ ID NO: 29) and HSV1.62186-62150 CTCCTCAACCCCGG TCTCCAACCCTCCCCTTGACCGTCGCCG (SEQ ID NO: 30) and subcloned into pBS-KS:ΔSacI. The plasmid insert was verified by sequence analysis. To obtain pBS-KS:ΔSacI, the SacI site was deleted from the polylinker of plasmid vector pBluescript-KS+, by digesting the plasmid with SacI.

Representative results of growth experiments of the kind described above (but testing different recombinant viruses in different cell types) were disclosed, e.g., in Bloom et al. (2015) (FIGS. 2 and 3). In the instantly described growth experiments, recombinant RCCHVs of the present disclosure are expected replicate with similar efficiency as wildtype virus 17syn+ in the epidermal cells that had been heat-treated and, in the case of HSV-GS1A or HSV-GS3A-C had been exposed to mifepristone. Essentially no replication of RCCHVs should be apparent in cultures that were not heat-treated or, in the case of HSV-GS1A or HSV-GS3A-C viruses had not also been exposed to mifepristone. In the neural cells, in which 17syn+ will replicate well, replication of RCCHVs should not be observed, regardless of whether the cultures were heat-treated and/or exposed to mifepristone.

Example 9: Reactivation from Latency

Herpesviruses are known to latently infect sensory nerve cells in which they can reactivate under adverse circumstances, e.g., during a high fever. In the RCCHVs of the present disclosure the replication-essential UL38 gene is controlled by a KRT1 or KRT77 promoter, which promoters are essentially inactive in nerve cells. Hence, reactivation of RCCHVs in sensory neurons should not occur in a subject, even if the subject is experiencing a high fever or other severe stress and, in the case of an HSV-GS1A or HSV-GS3A-C recombinant, is concurrently administered an antiprogestin. This assumption is tested in a well-established mouse model of heat-induced reactivation (Sawtell and Thompson (1992) J Virol 66: 2150-2156). In this model, all mice that had been inoculated on the lightly abraded rear footpads with HSV-1 wildtype virus strain 17syn+ were found to contain latent virus in their ganglia at 30 days after inoculation. No spontaneous reactivation was observed. Heat treatment reactivated virus in the dorsal root ganglia (DRG) in about 80% of latently infected animals.

In an exemplary experiment to demonstrate that RCCHV HSV-GS3A does not reactivate, 4 groups (n=10) of 4- to 6-week-old Swiss Webster mice are inoculated on the abraded rear footpads with 250 pfu of wildtype HSV-1 strain 17syn+(2 groups) or 50,000 pfu of HSV-GS3A (2 groups). Thirty days later, all animals will receive mifepristone (0.5 mg/kg) intraperitoneally, and one of the 17syn+ groups and one of the HSV-GS3B groups are subjected to heating in a 43° C. water bath as described in Sawtell and Thompson (1992). Individual animals or small groups are slowly lowered into the water. Body temperature increase is monitored by means of a rectally inserted thermocouple. Heat treatments are for 10 min (with body temperature reaching 43° C. after about 7 min). The mice are then allowed to recover at 37° C. for 15 min. Twenty-four hours later, all animals are euthanized. Dorsal root ganglia (DRG) are recovered, homogenized and subjected to a freeze-thaw cycle to lyse cells. After clarification, the extracts are used to infect confluent cultures of pICP8- and pUL38FBpCl-co-transfected E5 cells. The cultures are then monitored daily for cytopathic effects (reactivation).

Example 10: Vaccination Against Herpes Disease—an Immunization/Challenge Experiment Previous immunization/challenge experiments demonstrated that immunization with replication-competent controlled viruses such as HSV-GS3 induced a strong protective response against challenge with wildtype herpesvirus. The following exemplary experiment is performed to demonstrate that RCCHVs of the present disclosure are similarly capable of protecting against disease caused by a subsequent herpesvirus infection. Induction of protective immunity is evaluated in a mouse footpad lethal challenge model (McKendall (1977) Infect Immun 16: 717-719). Viruses HSV-GS3A, HSV-GS3 and KD6 (an ICP4$^-$ replication-incompetent HSV-1 recombinant (Dobson et al. 1990. Neuron 5:353-360) or vehicle are administered under anesthesia to the plantar surfaces of both rear feet of adult Swiss Webster outbred female mice (50,000 PFU per animal; 20 animals per group). Concurrently, and again 24 h later, the animals of one of the HSV-GS3A groups and one of the HSV-GS3 groups will receive an intraperitoneal injection of 50 μg/kg of body weight ulipristal (an antiprogestin). Three hours after inoculation, the mice in these groups are subjected to heat treatment (44.5° C. for 10 min) by immersion of their hind feet in a temperature-controlled water bath. Three weeks later, all animals will be reinoculated with 50,000 PFU/animal of the recombinant virus they had received before (or with vehicle for the mock group). The animals in the HSV-GS3A and HSV-GS3 groups will be exposed to ulipristal and subjected to heat treatment as before. Three weeks later, all the animals are challenged with a 20-fold lethal dose of the HSV-1 wild-type strain 17syn+ administered by the same route as the immunizing viruses. Survival of the animals is followed until no more lethal endpoints are reached, i.e., until all surviving animals have fully recovered. As is known from our previous experiments, replication-defective virus KD6 will induce a modest level of immunity. Unactivated HSV-GS3 will provide a comparable degree of protection. In contrast, activated (i.e., heat-treated in the presence of antiprogestin) HSV-GS3 will produce complete or near complete protective effect. It is expected that HSV-GS3A will perform essentially as HSV-GS3.

Example 11: Vaccination Against Influenza Disease—an Immunization/Challenge Experiment Previous immunization/challenge experiments demonstrated that immunization with replication-competent controlled viruses such as HSV-GS11 induced a strong protective response against challenge with wildtype influenza virus. The following exemplary experiment is performed to demonstrate that RCCHVs of the present disclosure expressing an antigen from another pathogen are capable of protecting against disease caused by infection with that pathogen. As does HSV-GS11, RCCV HSV-GS3C expresses a hemagglutinin (HA) gene from influenza virus A/Equine/Prague/1/56 (H7N7).

Viruses HSV-GS3C, HSV-GS11 and HSV-GS3 (negative control) or vehicle are administered under anesthesia to the plantar surfaces of both rear feet of adult female BALB/c mice (250,000 PFU virus per animal; 20 animals per group). Concurrently, and again 24 h later, the animals will receive an intraperitoneal injection of 50 μg/kg of body weight ulipristal. Three hours after inoculation, the mice are subjected to heat treatment (44.5° C. for 10 min) by immersion of their hind feet in a temperature-controlled water bath. Three weeks later, all animals will be reinoculated with 250,000 PFU/animal of the recombinant virus they had received before (or vehicle) as well as will be exposed to ulipristal and subjected to heat treatment as before. Three weeks later, all animals are challenged with a several-fold lethal dose of A/Equine/Prague/1/56 that is administered intranasally. Animals are observed until no more lethal endpoints (>20% weight loss) are reached, i.e., until all surviving animals are recovering. As is known from our previous experiments, HSV-GS11 will provide essentially complete protection against the influenza virus challenge, and HSV-GS3 will have at most a marginal protective effect. It is expected that HSV-GS3C will perform essentially as HSV-GS11.

Generally known molecular biology and biochemistry methods are/were used. Molecular biology methods are described, e.g., in "Current protocols in molecular biology", Ausubel, F. M. et al., eds., John Wiley and Sons, Inc. ISBN: 978-0-471-50338-5.

The invention claimed is:

1. A heat-controlled or heat- and small-molecule regulators-controlled replication-competent controlled alpha-herpesvirus whose replication can be transiently activated in nonneural cells infected with said replication-competent controlled alpha-herpesvirus but that cannot be transiently activated in neural cells infected with said replication-competent controlled alpha-herpesvirus, wherein the replication-competent controlled alpha-herpesvirus is a recombinant alpha-herpesvirus derived from a virus of the group consisting of a herpes simplex virus type 1 (HSV-1), a herpes simplex virus type 2 (HSV-2) and a varicella-zoster virus, said replication-competent controlled alpha-herpesvirus comprising:
   (a) a first heterologous promoter that is a nucleic acid sequence that acts as a heat shock promoter, the first heterologous promoter controlling the expression of a first replication-essential gene of the replication-competent controlled alpha-herpesvirus, wherein
      (1) the first heterologous promoter is functionally linked to the first replication-essential gene of the replication-competent controlled alpha-herpesvirus, or
      (2) the first heterologous promoter is functionally linked to a gene for a heterologous, unregulated or small-molecule-regulated transactivator that has been inserted in the genome of the replication-competent controlled alpha-herpesvirus and the first replication-essential gene is functionally linked to a promoter that is responsive to the transactivator, and
   (b) a second heterologous promoter that is known to be active in nonneural cells of a mammalian subject to which the replication-competent controlled alpha-herpesvirus is to be administered but is also known to be essentially inactive in neural cells of the mammalian subject, the second heterologous promoter being functionally linked to a second replication-essential gene of the replication-competent controlled alpha-herpesvirus.

2. The replication-competent controlled alpha-herpesvirus according to claim 1, wherein the second heterologous promoter is active in a cutaneous or subcutaneous region, or a mucosal membrane.

3. The replication-competent controlled alpha-herpesvirus of claim 1, wherein the replication-competent controlled alpha-herpesvirus is an HSV-1 or HSV-2 and is lacking a functional ICP47 gene.

4. The replication-competent controlled alpha-herpesvirus of claim 1, further comprising at least one of an expressed gene from another pathogen, an expressed heterologous gene encoding an immune-modulatory polypeptide and an expressed heterologous gene encoding another polypeptide.

5. The replication-competent controlled alpha-herpesvirus of claim 4, wherein the expressed gene from another pathogen is a gene encoding an influenza virus surface antigen, an internal protein or parts thereof.

6. The replication-competent controlled alpha-herpesvirus of claim 4, wherein the expressed gene from another pathogen is a gene encoding a human immunodeficiency virus surface antigen, an internal protein or parts thereof.

7. The replication-competent controlled alpha-herpesvirus of claim 1, wherein the second heterologous promoter is selected from the promoters of a KRT1, a KRT4, a KRT5, a KRT6A, a KRT10, a KRT11, a KRT13, a KRT77, an MLANA and a TYR gene.

8. The replication-competent controlled alpha-herpesvirus according to claim 4, wherein replication-competent controlled alpha-herpesvirus further comprises a gene encoding a cytokine.

9. The replication-competent controlled alpha-herpesvirus according to claim 4, wherein replication-competent controlled alpha-herpesvirus further comprises a gene encoding IL-4, IL-2 or GM-CSF.

10. A vaccine composition comprising an effective amount of the replication-competent controlled alpha-herpesvirus of claim 1 and a pharmaceutically acceptable carrier or excipient.

11. A method for vaccinating a subject against herpetic disease caused by an alpha-herpesvirus comprising administering the replication-competent controlled alpha-herpesvirus of claim 1 to a site in the skin of the subject and administering an activating heat dose to the administration site, wherein the herpetic disease is caused by the alpha-herpesvirus from which the replication-competent controlled alpha-herpesvirus was derived.

12. A method for vaccinating a subject against disease caused by another pathogen comprising administering the replication-competent controlled alpha-herpesvirus of claim 1 further comprising an expressed gene from the other pathogen to a site in the skin of the subject and administering an activating heat dose to the administration site.

* * * * *

SEQUENCE LISTING

<160> NUMBER OF SEQ ID NOS: 30

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
ctgactggct ttagcccctt                                           20

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
gccttagaga gaggtgagag c                                         21

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
gccacaaaac actttcaggt acata                                     25

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
tgatgcctta gagagaggtg a                                         21

<210> SEQ ID NO 5
<211> LENGTH: 25
<212> TYPE: DNA
<213> ORGANISM: Artificial Sequence
<220> FEATURE:
<223> OTHER INFORMATION: primer

<400> SEQUENCE: 5
aagatttatt agtgcgtttt ggtgc                                     25

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
cagaagcact ggtagcaagg a                                         21

<210> SEQ ID NO 7
<211> LENGTH: 1400
<212> TYPE: DNA
<213> ORGANISM: Mus musculus

<400> SEQUENCE: 7

```
aggatctgac acgctgtcct tagctaggca ccgtcagtta caccccaggt ggacttaacc    60
acccatgaag atgtggggga gcttttcaga cctcatgcct caccttttctc atttacaaat   120
gggtagactg atactattct caaacttcta tgaacattca cttacaacat ataagccaca   180
aaacactttc aggtacataa ccaattcctg actggcttta gccccttccc gcatcctgac   240
ccctgccatc atagtcgcca ccaactctta gaaacaccgc aagcttctca ggtcaggttt   300
tccagatttt cataactgct tcctcttcca aacccacact tatctcttct atggttcagc   360
gtgaggtgag gtttgaatct gtcatgcctc aactacccca ctccgctttg ccacacgtgc   420
cagtgccgac gtaccccacc agtccatgca cttttttataa tggcatttgc aagctgccta   480
ttttcaactg ctagcctctt atgcctgctg ttcctcattt gaagaggaac aagcaggaag   540
cccaggaaag tatacgccat tcccttggtg cttctagccc acccaccct ccatcctgct     600
tagtgacagc tgccccttct ttaatcgatc agcgaggtgc atttgaaaac ttattctaga   660
aaacattgga ttttttttcc tttgctctgt gtcaggagat gtgatttggt gaaccctggg   720
gtttgaaggg acaagtctca gaaatggatg aggaaaggaa atccctcctt tagggattca   780
agctcgactg agcacacctg ttactcaagg aaccgacaat accctagtga gtgtgtgggc   840
atgtgagccc atgagctggg gattacagct cgacagtgct ggggggttacg aaatcctatc   900
aagagtcacc aagaagtcag tgtggggggtc ctactttctc aaagtcacag acactctgaa   960
gagagatcct gtctgataaa gaaagtgatt accacacgag ccattcttgt ctgcacagca  1020
attctgagag cccatcctgg gagctaggtg tgtagtgttt atcgtattgt tgaggctcgt  1080
aaaaatcttg tatggctgca ggcgagccaa accctttgca ggctttgcat ctccggctga  1140
ctctgaggac caagcccaat ttcttctcag tatataaggg cacggcactg ggctcaaggc  1200
agaggagttc tcagctcctt ccatctcttg tctttgctct cacctctctc taaggcatca  1260
tgagtctaca gtgtagctcc aggtccctgt gccgcggtgg cggtggcagc aggaacttca  1320
gctcaggctc tgctggccta gtcagcttcc agcgcagatc caccagcagc tctatgcgcc  1380
gcagcggtgg aggtggtggt                                              1400
```

<210> SEQ ID NO 8
<211> LENGTH: 1400
<212> TYPE: DNA
<213> ORGANISM: Mus musculus

<400> SEQUENCE: 8

```
aaaaagaaca ttaggagaaa atgttccaca atctgcaaga gagcgattta aattccccca    60
tgttgagctg agcagcaacc ctttgcaaca ttgtataatg attcttctgg accggctatg   120
cttttcttctg gttttaaaca attgtgtcca tgtgggcaaa tcattgatca ttattttctg   180
aagctgggaa tttattcttt ctcttcatga tcacaagatt tattagtgcg ttttggtgca   240
gttgggtgtg aatatgggaa tgaagagaac gaacatgcac tagctatttg tgtccaagtg   300
caaacacaca cttctgttgg acaacacttg tagactctca tgaacttcac attacgtctt   360
ctgctgggac agcccttttct tctcagagag tgcgcatgag ccaaggttcc tttcctacta   420
ctccctgata agtacagaag gtgagagtaa tgctttaaga actcactatt attgttactg   480
tctctgccag gagaaaaatt ttatgctgac caaataataa tactaaatcc aaattaaggc   540
ttgtgtttca catacctgtg gtctttatgt atttcttaaa agatagctac ttttttctttt   600
```

-continued

```
tacaaaaata ttgtcggtgc cagtttagaa atattagaat agaagaagac atatgggagt    660
agttctcctc tgagtctagg agacattcat actgggagat gctcacagat attttgttca    720
cacacatgca tgcacacacc aaacaaacaa acaaacaaac aaaaaaccac aaaacaaaaa    780
atggattta tgtacgagga cagccttgtt acagcaagtg tctccactct catccaagct     840
gtggccccaa ggtcactaga cacttcatag ttttatccta gatctctctg gcacacccca    900
aaacaaacaa ctccatgctg cttcttagga aaagatcaat ttgagattta aggagaaaca    960
ctacaggagt ttccaacact gagatcctga gagattgcta tcctttggtc tctccgtagt   1020
aagagatgaa tgataaatga tcaagttggg ggagtttgtc tgcaatgcca tttcagcaac   1080
acataggtat gaggcttgta agcagatgct actggcaggc aaatactccc ctcccagggt   1140
tcggaaagtt tccagcccag caggtgtgtg tatatatagg gactgagcca gatcctttcc   1200
aagagagtcg cagctccctc agtccctgct ctctgcctgc tttcagctga gtccttgcta   1260
ccagtgcttc tggttgccct agcaaccatg agccgccagt ttagttctca gtctgcattt   1320
agctcgagga gcaggagggc ctatagctcc aggtcttcat caggctttgg aggtgggaga   1380
caggctctgg tgtctgtgag                                                1400

<210> SEQ ID NO 9
<211> LENGTH: 27
<212> TYPE: DNA
<213> ORGANISM: Artificial Sequence
<220> FEATURE:
<223> OTHER INFORMATION: primer for amplification of HSV-1 DNA

<400> SEQUENCE: 9
gagctcatca ccgcaggcga gtctctt                                          27

<210> SEQ ID NO 10
<211> LENGTH: 27
<212> TYPE: DNA
<213> ORGANISM: Artificial Sequence
<220> FEATURE:
<223> OTHER INFORMATION: primer for amplification of HSV-1 DNA

<400> SEQUENCE: 10
gagctcggtc ttcgggacta atgcctt                                          27

<210> SEQ ID NO 11
<211> LENGTH: 26
<212> TYPE: DNA
<213> ORGANISM: Artificial Sequence
<220> FEATURE:
<223> OTHER INFORMATION: primer for amplification of HSV-1 DNA

<400> SEQUENCE: 11
ggggtaccgg ttttgttttg tgtgac                                           26

<210> SEQ ID NO 12
<211> LENGTH: 26
<212> TYPE: DNA
<213> ORGANISM: Artificial Sequence
<220> FEATURE:
<223> OTHER INFORMATION: primer for amplification of HSV-1 DNA

<400> SEQUENCE: 12
ggggtaccgg tgtgtgatga tttcgc                                           26

<210> SEQ ID NO 13
<211> LENGTH: 21
```

```
<212> TYPE: DNA
<213> ORGANISM: Artificial Sequence
<220> FEATURE:
<223> OTHER INFORMATION: primer

<400> SEQUENCE: 13
tcgacaactc cgagtttcag c                                        21

<210> SEQ ID NO 14
<211> LENGTH: 40
<212> TYPE: DNA
<213> ORGANISM: Artificial Sequence
<220> FEATURE:
<223> OTHER INFORMATION: primer

<400> SEQUENCE: 14
ctcctcgcgg ccgcatcgat ccatagagcc caccgcatcc                    40

<210> SEQ ID NO 15
<211> LENGTH: 43
<212> TYPE: DNA
<213> ORGANISM: Artificial Sequence
<220> FEATURE:
<223> OTHER INFORMATION: primer

<400> SEQUENCE: 15
ctcctcaagc ttctcgagca cacggagcgc ggctgccgac acg                43

<210> SEQ ID NO 16
<211> LENGTH: 35
<212> TYPE: DNA
<213> ORGANISM: Artificial Sequence
<220> FEATURE:
<223> OTHER INFORMATION: primer

<400> SEQUENCE: 16
ctcctcggta ccccatggag gccagcagag ccagc                         35

<210> SEQ ID NO 17
<211> LENGTH: 42
<212> TYPE: DNA
<213> ORGANISM: Artificial Sequence
<220> FEATURE:
<223> OTHER INFORMATION: primer

<400> SEQUENCE: 17
ctcctcgcgg ccgcactagt tccgcgtgtc cctttccgat gc                 42

<210> SEQ ID NO 18
<211> LENGTH: 58
<212> TYPE: DNA
<213> ORGANISM: Artificial Sequence
<220> FEATURE:
<223> OTHER INFORMATION: primer

<400> SEQUENCE: 18
ctcctcctcg agaagcttat gcatgagctc gacgtctcgg cggtaatgag atacgagc    58

<210> SEQ ID NO 19
<211> LENGTH: 32
<212> TYPE: DNA
<213> ORGANISM: Artificial Sequence
<220> FEATURE:
<223> OTHER INFORMATION: primer

<400> SEQUENCE: 19
```
ctcctcagaa cccaggacca gggccacgtt gg                                32

<210> SEQ ID NO 20
<211> LENGTH: 33
<212> TYPE: DNA
<213> ORGANISM: Artificial Sequence
<220> FEATURE:
<223> OTHER INFORMATION: primer

<400> SEQUENCE: 20
ctcctcatgg agacaaagcc caagacggca acc                               33

<210> SEQ ID NO 21
<211> LENGTH: 36
<212> TYPE: DNA
<213> ORGANISM: Artificial Sequence
<220> FEATURE:
<223> OTHER INFORMATION: primer

<400> SEQUENCE: 21
ctcctcggag accggggttg gggaatgaat ccctcc                            36

<210> SEQ ID NO 22
<211> LENGTH: 35
<212> TYPE: DNA
<213> ORGANISM: Artificial Sequence
<220> FEATURE:
<223> OTHER INFORMATION: primer

<400> SEQUENCE: 22
ctcctcgcgg ggcgtgggag gggctggggc ggacc                             35

<210> SEQ ID NO 23
<211> LENGTH: 36
<212> TYPE: DNA
<213> ORGANISM: Artificial Sequence
<220> FEATURE:
<223> OTHER INFORMATION: primer

<400> SEQUENCE: 23
ggactgacgt caagatttat tagtgcgttt tggtgc                            36

<210> SEQ ID NO 24
<211> LENGTH: 30
<212> TYPE: DNA
<213> ORGANISM: Artificial Sequence
<220> FEATURE:
<223> OTHER INFORMATION: primer

<400> SEQUENCE: 24
caacccgggc agaagcactg gtagcaagga                                   30

<210> SEQ ID NO 25
<211> LENGTH: 30
<212> TYPE: DNA
<213> ORGANISM: Artificial Sequence
<220> FEATURE:
<223> OTHER INFORMATION: primer

<400> SEQUENCE: 25
ggactgacgt ctgactggct ttagcccctt                                   30

<210> SEQ ID NO 26
<211> LENGTH: 29
<212> TYPE: DNA
<213> ORGANISM: Artificial Sequence

```
<220> FEATURE:
<223> OTHER INFORMATION: primer

<400> SEQUENCE: 26
caacccgggc cttagagaga ggtgagagc                                      29

<210> SEQ ID NO 27
<211> LENGTH: 2039
<212> TYPE: DNA
<213> ORGANISM: Homo sapiens
<220> FEATURE:
<221> NAME/KEY: misc_feature
<222> LOCATION: (3)..(3)
<223> OTHER INFORMATION: n is a, c, g, or t

<400> SEQUENCE: 27
cgntgctcgt tacttagctt gttaccatgg atctgcccgt gggccccggc gcggcggggc    60
ccagcaacgt cccggccttc ctgaccaagc tgtggaccct cgtgagcgac ccggacaccg   120
acgcgctcat ctgctggagc ccgagcggga acagcttcca cgtgttcgac cagggccagt   180
ttgccaagga ggtgctgccc aagtacttca agcacaacaa catggccagc ttcgtgcggc   240
agctcaacat gtatggcttc cggaaagtgg tccacatcga gcaggcggc ctggtcaagc   300 cagagagaga cgacacggag ttccagcacc catgcttcct gcgtggccag gagcagctcc   360
ttgagaacat caagaggaaa gtgaccagtg tgtccaccct gaagagtgaa gacataaaga   420
tccgccagga cagcgtcacc aagctgctga cggacgtgca gctgatgaag gggaagcagg   480
agtgcatgga ctccaagctc ctggccatga gcatgagaa tgaggctctg tggcgggagg   540
tggccagcct tcggcagaag catgcccaga acagaaagtc gtcaacaagc tcattcagtt   600
cctgatctca ctggtgcagt caaaccggat cctgggggtg aagagaaaga tccccctgat   660
gctgaacgac agtggctcag cacattccat gcccaagtat agccggcagt tctccctgga   720
gcacgtccac ggctcgggcc cctactcggc cccctcccca gcctacagca gctccagcct   780
ctacgcccct gatgctgtgg ccagctctgg acccatcatc tccgacatca ccgagctggc   840
tcctgccagc cccatggcct ccccggcgg gagcatagac gagaggcccc tatccagcag   900 cccccctggtg cgtgtcaagg aggagccccc cagcccgcct cagagccccc gggtagagga   960
ggcgagtccc gggcgccat cttccgtgga caccctcttg tccccgaccg ccctcattga  1020
ctccatcctg cgggagagtg aacctgcccc cgcctccgtc acagccctca cggacgccag  1080
gggccacacg gacaccgagg ccggcctcc ctcccccccg cccacctcca ccctgaaaa  1140 gtgcctcagc gtagcctgcc tggacaagaa tgagctcagt gaccacttgg atgctatgga  1200
ctccaacctg gataacctgc agaccatgct gagcagccac ggcttcagcg tggacaccag  1260
tgccctgctg gacctgttca gcccctcggt gaccgtgccc gacatgagcc tgcctgacct  1320
tgacagcagc ctggccagta tccaagagct cctgtctccc caggagctcc ccaggcctcc  1380
cgaggcagag aacagcagcc cggattcagg gaagcagctg gtgcactaca cagcgcagcc  1440
gctgttcctg ctggaccccg gctccgtgga caccgggagc aacgacctgc cggtgctgtt  1500
tgagctggga gagggctcct acttctccga aggggacggc ttcgccgagg accccaccat  1560
ctccctgctg acaggctcgg agcctcccaa agccaaggac cccactgtct cctagaggcc  1620
ccggaggagc tgggccagcc gcccaccccc accccagtg cagggctggt tttggggagg  1680
cagggcagcc tcgcggtttt gggcactggt gggtcggccg ccatagcccc agtaggacaa  1740
acgggctcgg gtctgggcag cacctctggt caggagggtc accctggcct gccagtctgc  1800
```

```
cttcccccaa ccccgtgtcc tgtggtttgg ttggggcttc acagccacac ctggactgac   1860
cctgcaggtt gttcatagtc agaattgtat tttggatttt tacacaactg tcccgttccc   1920
cgctccacag agatacacag atatatacac acagtggatg gacggacaag acaggcagag   1980
atctataaac agacaggctt taaaaaaaaa aaaaaaaaa aaaaaaaaaa aaaaaaccc    2039

<210> SEQ ID NO 28
<211> LENGTH: 29
<212> TYPE: DNA
<213> ORGANISM: Artificial Sequence
<220> FEATURE:
<223> OTHER INFORMATION: primer

<400> SEQUENCE: 28
gacggtaccc cgaccttgac agcagcctg                                      29

<210> SEQ ID NO 29
<211> LENGTH: 42
<212> TYPE: DNA
<213> ORGANISM: Artificial Sequence
<220> FEATURE:
<223> OTHER INFORMATION: primer

<400> SEQUENCE: 29
ctcctcttta ttttacacac attccccgcc ccgccctagg tt                       42

<210> SEQ ID NO 30
<211> LENGTH: 42
<212> TYPE: DNA
<213> ORGANISM: Artificial Sequence
<220> FEATURE:
<223> OTHER INFORMATION: primer

<400> SEQUENCE: 30
ctcctcaacc ccggtctcca accctcccct tgaccgtcgc cg                       42
```